Figure 1A:
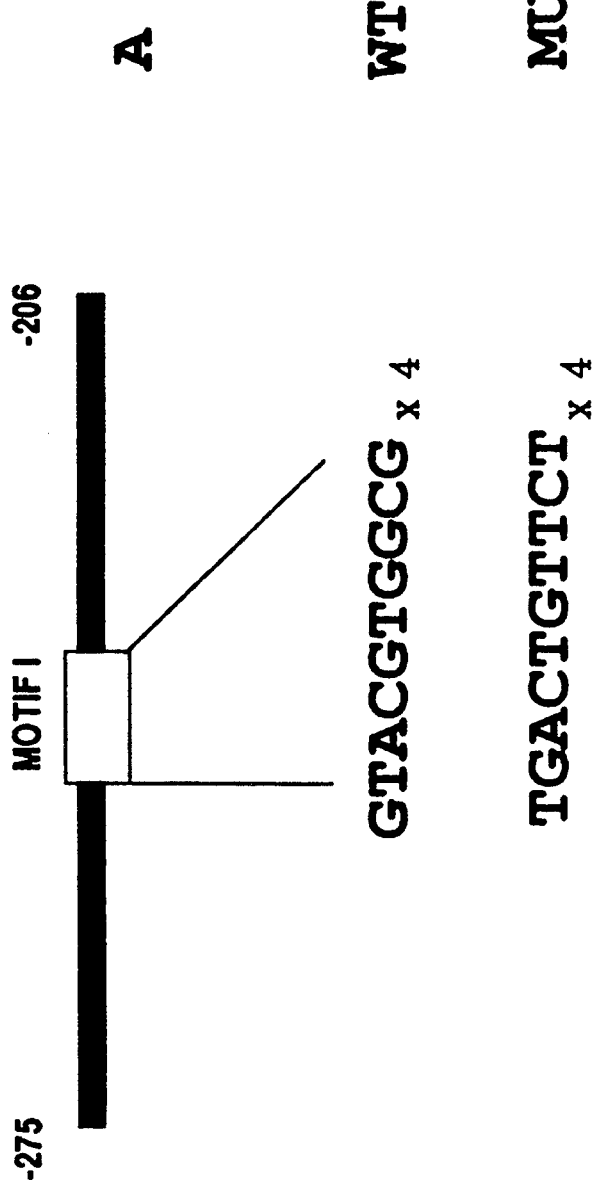

United States Patent [19]

Chua

[11] Patent Number: 5,362,864
[45] Date of Patent: Nov. 8, 1994

[54] TRANS-ACTIVATING FACTOR-1

[75] Inventor: Nam-Hai Chua, Scarsdale, N.Y.

[73] Assignee: The Trustees of the Rockefeller University, New York, N.Y.

[21] Appl. No.: 651,710

[22] Filed: Feb. 6, 1991

[51] Int. Cl.$^5$ .................... C07H 21/04; C12N 15/29; C12N 15/67
[52] U.S. Cl. .................. 536/23.6; 536/23.6; 536/24.1; 435/172.3; 435/240.4; 435/252.3; 800/205; 935/35; 935/36
[58] Field of Search ............ 536/27; 435/240.4, 252.3; 800/205; 935/35, 36

[56] References Cited

U.S. PATENT DOCUMENTS 4,833,080  5/1989  Brent et al. ............ 435/172.3

OTHER PUBLICATIONS

Salinas et al., 1992, The Plant Cell 4: 1485–1493.
Mundy and Chua, 1988, EMBO J. 7(8):2279–2286.
Yamaguchi-Shinozaki, et al. 1989 Plant Molecular Biology 14:29–39.
Mundy, et al. 1990, Proc. Natl. Acad. Sci. 87: 1406–1410.
Baker et al., 1988, Plant Molecular Biology 11:277–291.
Marcotte, Jr., 1988, Nature 335:454–457.
Dure, et al., 1989, Plant Molecular Biology 12:475–486.
Marcotte, et al., 1989, The Plant Cell 1:969–976.
Guiltinan, et al., 1990, Science 250:267–271.
Hilson et al. 1990 (Jul.) The Plant Cell 1:651–658.
Ma et al. 1988 Nature 334:631–633.
Oeda et al. 1991 (Aug.) EMBO Journal 10:1793–1802.
Tabata et al. 1989 (Sep.) Science 245:965–967.

Primary Examiner—Patricia R. Moody
Attorney, Agent, or Firm—Pennie & Edmonds

[57] ABSTRACT

The active portion of a trans-activating factor, TAF-1, has been identified, isolated and characterized. This proteinaceous factor binds to motif-I-like sequences previously identified within numerous plant promoter elements. TAF-1 may be engineered into cell culture systems or transgenic plants to increase or modulate the expression of heterologous genes fused to promoter elements containing one or more copies of cis-acting sequences known to bind TAF-1.

27 Claims, 15 Drawing Sheets

```
  1                Ala His Gly Gly Val Tyr Ala His Pro Gly Val Pro Ile
  1     GG AAT TCC GCT CAT CGT GGC GTT TAT GCA CAT CCT GGA GTT CCA ATT

14     Gly Ser His Pro Pro Gly His Gly Met Ala Thr Ser Pro Ala Val Ser
 48     GGA TCT CAC CCT CCA GGA CAT GGG ATG GCA ACA TCT CCT GCT GTC AGC

30     Gln Ala Met Asp Gly Ala Ser Leu Ser Leu Asp Ala Ser Ala Lys Ser
 96     CAA GCC ATG GAT GGT GCT TCT TTG AGT TTG GAT GCA TCT GCT AAG TCT

46     Ser Glu Asn Ser Asp Arg Gly Leu Leu Ala Met Ser Leu Gly Asn Gly
144     TCA GAG AAT TCT GAT CGA GGC TTG CTG GCA ATG TCA CTA GGA AAT GGC

62     Ser Ala Asp Asn Ile Glu Gly Gly Ala Asp His Gly Asn Ser Gln Ser
192     AGT GCT GAC AAC ATT GAA GGT GGA GCG GAC CAT GGA AAT TCA CAG AGT

78     Gly Asp Thr Glu Asp Ser Thr Asp Gly Ser Asp Thr Asn Gly Ala Gly
240     GGG GAC ACT GAA GAT TCA ACT GAT GGA AGT GAC ACA AAT GGA GCT GGG

94     Val Ser Glu Arg Ser Lys Lys Arg Ser Arg Glu Thr Thr Pro Asp Asn
288     GTC AGT GAG AGA AGT AAG AAA CGA AGC CGT GAG ACA ACT CCT GAT AAC

110     Ser Gly Asp Ser Lys Ser His Leu Arg Arg Cys Gln Pro Thr Gly Glu
336     TCT GGT GAT AGT AAG AGT CAC TTA CGA CGA TGT CAA CCT ACT GGG GAA

126     Ile Asn Asp Asp Ser Glu Lys Ala Ile Val Ala Val Arg Pro Gly Lys
384     ATA AAT GAT GAT TCT GAG AAG GCA ATT GTG GCT GTT CGT CCT GGT AAG

142     Val Gly Glu Lys Val Met Gly Thr Val Leu Ser Pro Ser Met Thr Thr
432     GTA GGG GAG AAA GTG ATG GGA ACT GTA CTT TCT CCT AGC ATG ACA ACA

158     Thr Leu Glu Met Arg Asn Pro Ala Ser Thr His Leu Lys Ala Ser Pro
480     ACT TTG GAA ATG AGA AAT CCT GCT AGT ACA CAT TTG AAA GCT AGC CCA

174     Thr Asn Val Ser Gln Leu Ser Pro Ala Leu Pro Asn Glu Ala Trp Leu
528     ACT AAT GTT TCA CAA CTC AGC CCT GCA CTG CCA AAT GAA GCC TGG TTA

190     Gln Asn Glu Arg Glu Leu Lys Arg Glu Lys Arg Lys Gln Ser Asn Arg
576     CAG AAT GAA CGT GAG CTG AAG CGG GAG AAA AGG AAA CAG TCT AAT CGG
```

FIG. 2A

| | | | | | | | | | | | | | | |
|---|---|---|---|---|---|---|---|---|---|---|---|---|---|---|
| 206 | Glu | Ser | Ala | Arg | Arg | Ser | Arg | Leu | Arg | Lys | Gln | Ala | Glu | Ala | Glu | Glu |
| 624 | GAA | TCT | GCA | AGG | CGA | TCA | AGA | TTG | AGA | AAA | CAG | GCT | GAA | GCT | GAA | GAA |

| 222 | Leu | Ala | Ile | Arg | Val | Gln | Ser | Leu | Thr | Ala | Glu | Asn | Met | Thr | Leu | Lys |
| 672 | TTG | GCA | ATA | CGA | GTT | CAG | TCT | TTA | ACA | GCG | GAA | AAC | ATG | ACA | CTC | AAA |

| 238 | Ser | Glu | Ile | Asn | Lys | Leu | Met | Glu | Asn | Ser | Glu | Lys | Leu | Lys | Leu | Glu |
| 720 | TCT | GAG | ATA | AAC | AAA | TTA | ATG | GAG | AAC | TCA | GAG | AAA | CTG | AAG | CTA | GAA |

| 254 | Asn | Ala | Ala | Leu | Met | Glu | Arg | Leu | Lys | Met | Asn | Ser | *** | | | |
| 768 | AAT | GCT | GCT | TTA | ATG | GAG | AGA | CTG | AAA | ATG | AAC | AGC | TAG | GCC | AGA | CAG |

```
 816  AAG AAG TGA GTT TAG GTA AGA TTG ATG ATA AGA GGC TGC AAC CTG TAG

864  GCA CGG CAA ACC TAC TAG CAA GAG TCA ACA ACT CTG GTT CCT CGG ATA

912  GAG CAA ACG AGG AGA TTG AAG TTT ATG AGA ACA ATA GTT CTG GAG CAA

960  AGC TTC ATC AAC TAC TCG ATT CCA GTC CCA GAA CTG ATG CAG TGG CTG

1008  CTG GGT GAT CGA TGG TAC ACC CCC AAC TTT GAG ATC TTA CAT TTT AGT

1056  CTG ATT ATG TAA TTT TGG CGT AAT TAT AAG TCC AAA GTT ACT GCT AAC

1104  TGC GGG AGA GGA ACA GAA TGG AAC AGC TAA ATA GGA TTA TGG AAC TTA

1152  CGG GAT TCT AAT TTT ACC TAA TTG TAG TTT ACG TGT CGG AAG AAC TGA

1200  TGT GTG CTT TTA TAC TTT TCT TTT CTT CCC TTT TTC CCC CTT TTC ACC

1248  TCA GAG AGG GAT GTT GGC CAT AAT AGT TTA TGT AAG TTT GTA ATC TTC

1296  GAC ATG TAT AAG CTT TGA TTG AGG AAA AAA AAA AAA GGA ATT C
```

|     |            | BINDING |
|-----|------------|---------|
| PA  | GCCAC GTGGC | + + + + |
| M1  | GCaAC GTGGC | + +     |
| WT  | GgtAC GTGGC | +       |
| M5  | cgtAC GTGGg | +       |
| M2  | Ggttg GTGGC | −       |
| M3  | GgtAC caGGC | −       |
| M4  | GgtAC GTccC | −       |

FIG. 4C

FIG. 5A

| | | | | | | | | | | | | | | | | | | | | | |
|---|---|---|---|---|---|---|---|---|---|---|---|---|---|---|---|---|---|---|---|---|---|
| TAF-1 | (195-215) | K | R | E | K | R | K | Q | S | N | R | E | S | A | R | R | S | R | L | R | K |
| EmBP-1 | (105-125) | K | R | E | R | R | K | Q | S | N | R | E | S | A | R | R | S | R | L | R | K |
| HBP-1 | (254-274) | K | K | Q | K | R | K | L | S | N | R | E | S | A | R | R | S | R | L | R | K |
| OCSBF-1 | (26-46) | R | R | E | K | R | R | L | S | N | R | E | S | A | R | R | S | R | L | R | K |
| O2 | (228-248) | R | V | R | K | R | K | E | S | N | R | E | S | A | R | R | S | R | Y | R | K |
| TGA-1a | (87-107) | K | V | L | R | R | L | A | Q | N | R | E | A | A | A | R | K | S | R | L | R | K |
| TGA-1b | (185-205) | K | K | R | A | R | L | V | R | N | R | E | S | A | Q | L | S | R | Q | R | K |

FIG. 5B

| | | | * | | * | | * | | * | | * |
|---|---|---|---|---|---|---|---|---|---|---|---|
| TAF-1 | (216-258) | QAEAEEL | | AIQVQSL | | TAENNTL | | KSEINKL | | MENSEKL | | KLENAAL |
| EmBP-1 | (126-168) | QQECEEL | | AQKVSEL | | TAANGTL | | RSELDQL | | KKDCKTM | | ETENKQL |
| HBP-1 | (275-317) | QAECEEL | | GQRAEAL | | KSENSSL | | RIELDRI | | KKEYEEL | | LSKNTSL |
| OCSBF-1 | (47-68) | QQHLDEL | | VQEVARL | | QADNARV | | | | | | |

TRANS-ACTIVATING FACTOR-1

TABLE OF CONTENTS

1. Introduction
2. Background of the Invention
3. Summary of the Invention
   3.1 Definitions
4. Description of the Figures
5. Description of the Invention
   5.1 Structure of TAF-1
   5.2 Function of TAF-1
      5.2.1. TAF-1 Can Function as a Trans-Activator
      5.2.2. Relationship of TAF-1 to GBF and CG-1
      5.2.3. Function of TAF-1 in vivo
   5.3. Production of TAF-1
      5.3.1. The TAF-1 Coding Sequence
      5.3.2. Construction of Expression Vectors Containing The TAF-1 Coding Sequence
      5.3.3. Identification of Transfectants or Transformants Expressing The TAF-1 Gene Product and Isolation of TAF-1
   5.4 Use of TAF-1 to Increase Gene Expression
6. Example: Characterization of TAF-1
   6.1. Materials and Methods
      6.1.1. Isolation of TAF-1 Recombinant Phage
      6.1.2. Nucleotide Sequence Analyses
      6.1.3. Gel Mobility-Shift Assays
      6.1.4. Partial Purification of Recombinant TAF-1
      6.1.5. Northern and Southern Analysis
      6.1.6. Production of Transgenic Plants
      6.1.7. β-Glucuronidase (GUS) Enzyme Assays
      6.1.8. High Velocity Microprojectile Bombardment
   6.2. Results
      6.2.1. A Tobacco Factor Binds to the Conserved Motif I
      6.2.2. Isolation of A cDNA Clone Encoding a Protein Binding to Motif I
      6.2.3. DNA Binding Specificity of Truncated TAF-1
      6.2.4. Binding Site Sequence Specificity of TAF-1
      6.2.5. Binding Site Sequence Specificity of the Nuclear Motif I Factor
      6.2.6. Truncated TAF-1 Also Binds to the Hex Motif
      6.2.7. Expression Pattern of TAF-1 mRNA
      6.2.8. TAF-1 is a Trans-Activator

1. INTRODUCTION

The present invention relates to a transactivating factor, TAF-1, its production and use in trans to increase expression of genes containing the binding site for TAF-1. TAF-1 described herein may be used or engineered into cell culture systems or in transgenic plants to increase or modulate expression of the heterologous gene product.

2. BACKGROUND OF THE INVENTION

Recent investigations into plant genes have focused on sequence-specific DNA-binding proteins that may play a role in trans regulation. These DNA-binding proteins are usually localized in the nuclei, and their target DNA sequences and binding specifications can be characterized by gel mobility-shift assays and DNAse footprinting techniques using either whole cell or nuclear extracts. Results from such in vitro experiments have led to the conclusion that 5' upstream regions of plant genes contain binding sites for multiple nuclear protein factors (cf. Allen et al., 1989, Plant Cell 1:623–631; Gilmartin et al., 1990, Plant Cell 2, 369–378; Schindler and Cashmore, 1990, EMBO J. 9:3415–3427). Moreover, in some cases, a single nuclear factor may interact with more than one promoter. For example, the tobacco nuclear factor, Activation Sequence Factor (ASF)-I, was first identified by its ability to bind to the TGACG motifs located in the −83 to −63 region of the Cauliflower Mosaic Virus (CaMV) 35S promoter (Lam et al., 1989). Further analyses, however, demonstrated that it also binds to a similar motif in the 5' regions of the wheat histone H3 gene (Katagiri et al., 1989, Nature 340:727–730), nopaline synthase gene (Katagiri et al., 1989, supra; 1989 Bouchez, et al., 1989, EMBO J. 8, 4197–4204; Lam et al., 1990, J. Biol. Chem 265:9909–9913), octopine synthase gene (Fromm, et al. 1989, Plant Cell 1:977–984; Tokuhisa et al., 1990, Plant Cell 2:215–224), and the TR1' and 2' promoters of octopine T-DNA (Bouchez et al., 1989, EMBO J 8:4197–4204). These biochemical results are consistent with previous genetic data indicating that a regulatory gene may control the activity of several structural genes (cf. Coe and Neuffer, 1977, In Sprague, G. F., ed., Corn and Corn Improvement. Madison, Wis., USA. pp. 111–223).

Another nuclear factor, the G-box binding factor (GBF), also appears to bind to several classes of promoters. Giuliano et al., (1988, Proc. Natl. Acad. Sci. USA 85:7089-7093) first reported that this factor binds to the G-box motif, 5'-TCTTACACGTGGCAYY-3' (SEQ. ID NO: 27) conserved in the upstream sequences of several dicotyledonous rbcS genes. A G-box related motif, containing the core sequence CACGTG is also present in the 5' regions of two other classes of light-responsive genes: the Arabidopsis cab genes (Ha and An, 1988, Proc. Natl. Acad. Sci. USA 85:8017–8021) and the chalcone synthase gene (chs) of Petroselium crispum (Schulze-Lefert et al., 1989, EMBO J.8:651–656; Schulze-Lefert et al., 1989, Plant Cell 1:707–714) and Antirrhinum majus (Staiger, et al., 1989, Proc. Natl. Acad. Sci. USA. 86:6930–6934) have demonstrated that the G-box motif in chalcone synthase is related to that of N. tabacum rbcS since the two sequences appear to compete for the same tobacco nuclear factor, CG-1. Their results suggest that CG-1 and GBF have similar binding specificities; however, it is not known whether the two protein factors are indeed identical or, just related. It should be noted that the G-box or related motif is not exclusively associated with light-responsive genes because it is also found at −577 of the patatin (PI-II) promoter (Rosahl et al., 1986, Mol. Gen. Genet. 203:214–220) and at −200 of the Arabidopsis alcohol dehydrogenase (Adh) promoter (McKendree et al., 1990, Plant Cell 2:207–214; DeLisle and Ferl, 1990, Plant Cell 2:547–557). These findings raise the possibility that GBF or CG-1 may simply be an ubiquitous factor capable of interacting with promoters of diverse regulatory properties.

Recently, a rice nuclear factor that binds specifically to a 5'-GTACGTGGCG-3' sequence (SEQ. ID NO: 28) of the rice rab16A promoter has been described (Mundy et al., 1990, Proc. Natl. Acad. Sci. USA 87,406–410). This sequence, designated as motif I, is conserved not only among all four ABA-responsive rab16 genes (A-D; Mundy and Chua, 1988, EMBO J. 7:2279–2286; Yamaguchi-Shinozaki et al., 1990, Plant Mol. Biol. 14:29–39), but also in cotton genes (lea) that are expressed during late embryogenesis (Baker et al., 1988, Plant Molecular Biology 11:277–291) as well as the Em gene of wheat (Marcotte, et al., 1989, Plant Cell 1:969–976). Comparison of motif I and the G-box motif reveals extensive sequence homology.

3. SUMMARY OF THE INVENTION

The structure and function of a transcription activator factor, TAF-1, is described. TAF-1 binds to particular motifs of the rab promoter and can increase gene expression by trans-activating a gene of interest linked to a binding site for TAF-1.

The invention is illustrated by the examples described infra which demonstrate that tobacco nuclear extract contains a factor that binds to the rab16 motif I and that this binding is sensitive to competition by a G-box motif. A partial cDNA clone, isolated from a tobacco cDNA expression library is described which encodes a truncated protein (TAF-1) with similar DNA binding specifications as the nuclear motif I factor. Both the nuclear factor and the truncated TAF-1 show very high affinity binding to the G-box motif. TAF-1 contains an acidic domain at its N-terminus and at its C-terminus a basic domain contiguous to a leucine repeat; moreover, when expressed transiently in leaf cells, it can transactivate a β-glucuronidase (GUS) reporter gene linked to a motif I tetramer.

3.1 DEFINITIONS

The terms listed as used herein will have the indicated meanings:
ABA=abscisic acid
ABRE=ABA responsive element
GUS=β-glucuronidase
TAF=trans-activating factor

4. DESCRIPTION OF THE FIGURES

Figure 1B:
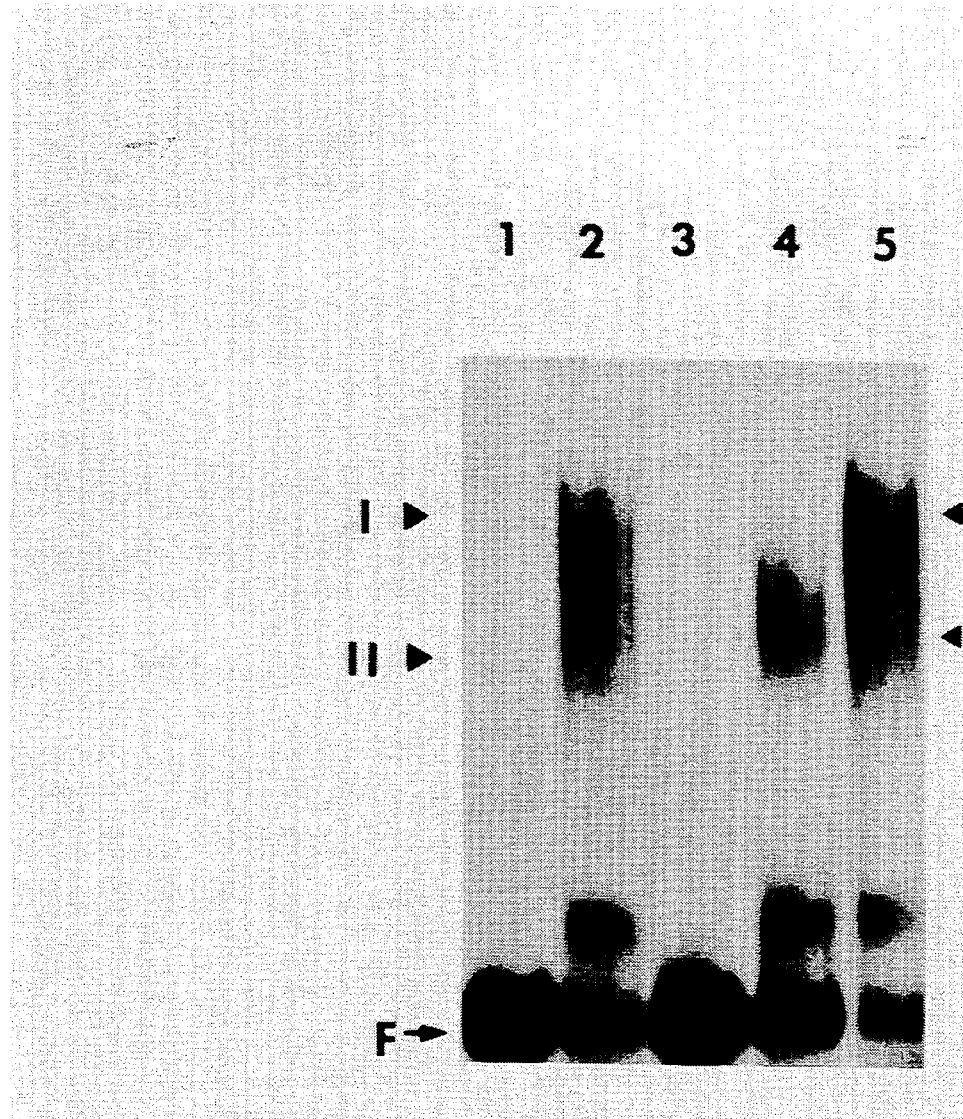

FIGS. 1A–1B. Tobacco nuclear extracts contain a binding activity for motif I of rice rab16 genes. FIG. 1A DNA probes used for gel mobility-shift assays. Probe A which is 70-bp long contains the sequences between −275 and −206 of the rice rab16B gene (Yamaguchi-Shinozaki et al., 1990, Plant Mol. Biol. 14, 29–39). The wild type probe contains four tandem copies of motif I, [CTACGTGGCG]GTACGTGGCG and the mutant (MU) probe (SEQ. ID NO: 3) contains four tandem copies of a mutant sequence of motif I in which the G's were changed to T's and the T's were changed to G's. FIG. 1B. Gel mobility shift assays of tobacco nuclear extract using probe A. Experiments were performed as described in Materials and Methods. Competitors were added at 300-fold molar excess. F, free probe; I and II, complex I and II, respectively; T. Ext., tobacco nuclear extract; comp., competitors. A, probe A. Arrowheads indicate positions of specific DNA-protein complexes.

Figure 2B:
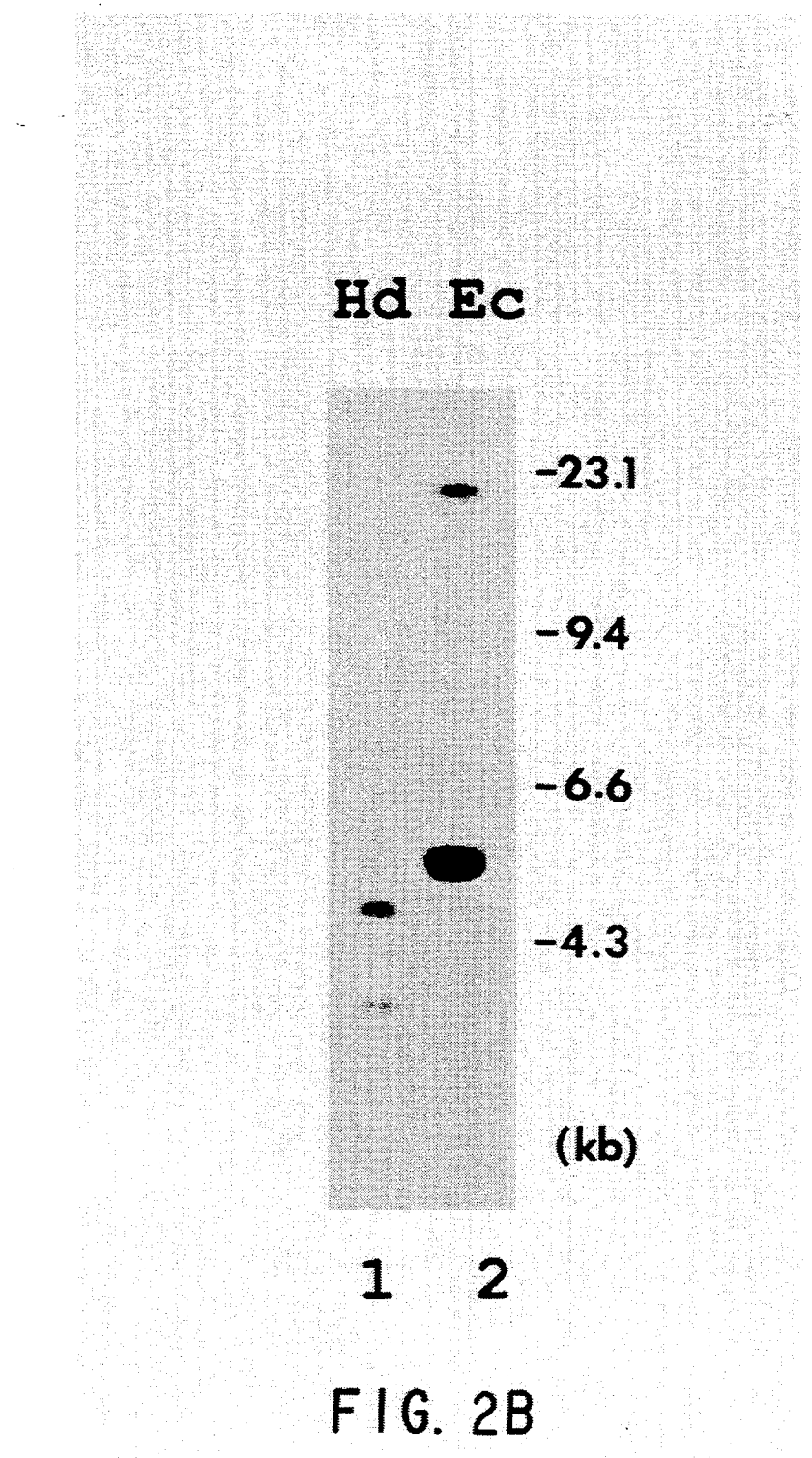
Figure 2C:
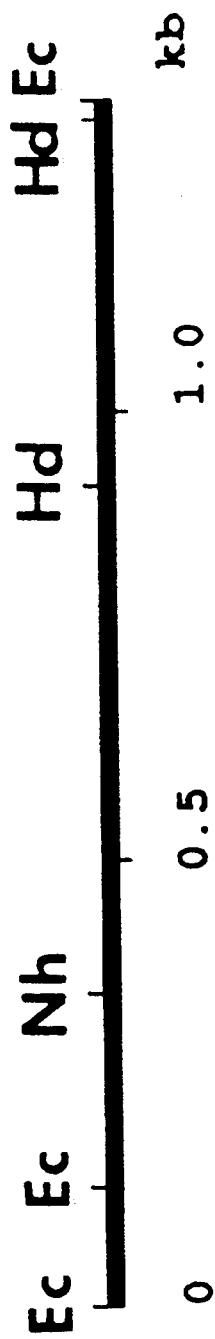
Figure 2D:
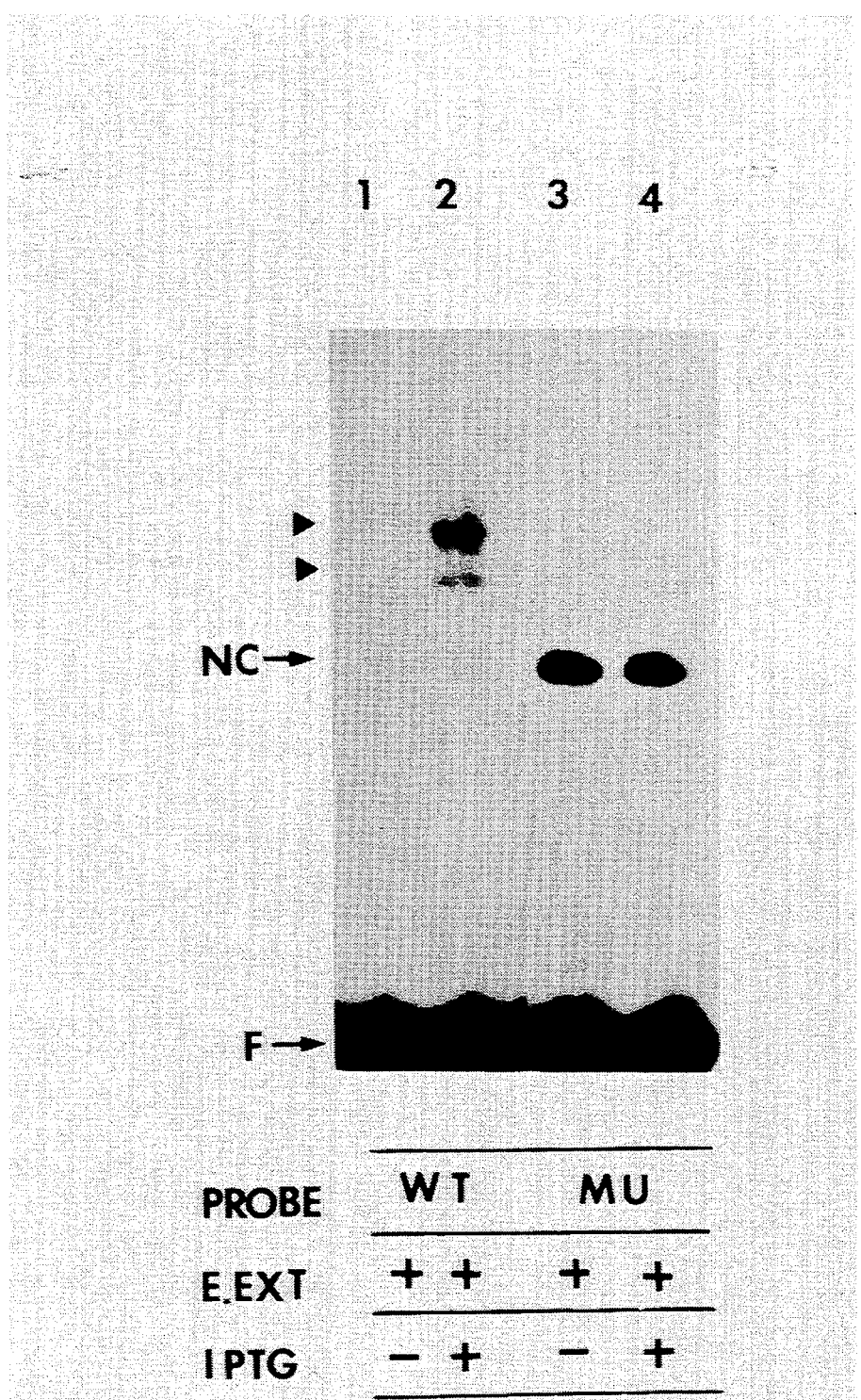

FIGS. 2A–2D. Characterization of the cDNA clone p5a and its encoded product (TAF-1). FIG. 2A. Nucleotide sequence (SEQ ID NO: 1) of clone 5a The partial cDNA is comprised of 1338 [1,345-bp] and contains an open reading frame of 265 [264] amino acids. The first methionine is located at position 22. FIG. 2B. Southern blot analysis of nuclear genes encoding TAF-1. High molecular weight tobacco DNA (10 µg) was digested with either HindIII (lane 1) or EcoRI (lane 2). The filter was hybridized to the larger EcoRI fragment (∼1.2 Kb) at the 3' end of the cDNA clone 5a. FIG. 2C. FIG. 2C. Restriction map of cDNA clone p5a. Hd, HindIII; Ec, EcoRI; Nh, NheI. FIG. 2D. DNA-binding specificity of the protein product encoded by clone 5a. The partial cDNA clone was placed downstream of the lacZ promoter in the vector pSK(−) and the recombinant plasmid was transformed into E. coli. In this expression vector, the Met-22 was presumably used as the initiator methionine to produce a truncated TAF-1 of Mr-26,000. Exponential phase cultures were induced with 2mM IPTG (+); uninduced cultures were used as controls (−). Extracts (E. ext) were prepared from induced (+) and uninduced (−) cultures and fractionated with ammonium sulfate as described in the Materials and Methods. SDS-PAGE analysis showed the presence of a 26,000-Kd polypeptide in extracts from the induced, but not the uninduced cultures. Gel mobility-shift assays were performed using the WT (SEQ. ID NO: 2). or the mutant motif (SEQ. ID NO: 3) I tetramer as probe (see FIG. 1A). F, free probe; NC, non-specific complex; arrowheads indicate specific complexes.

Figure 3:
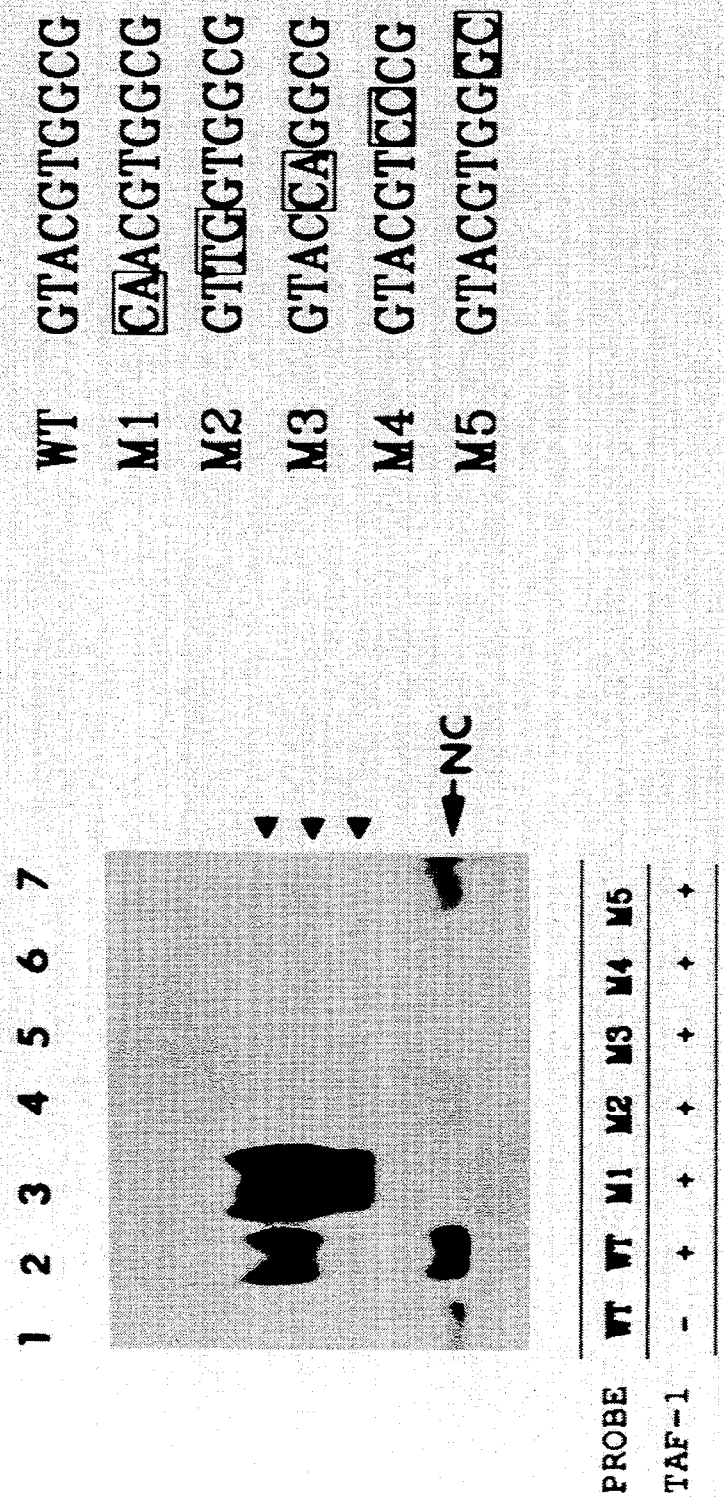

FIG. 3. Mutational analysis of motif I. Tetramers of WT motif I (SEQ. ID NO: 2) and of various mutants (M1 to M5) (SEQ. ID NO: 4–8) were assayed for their ability to interact with the recombinant TAF-1 produced in E. coli by gel mobility-shift. The mutants contained successive 2-bp alterations as indicated in the figure. NC, non-specific complex; arrowheads indicate specific complexes.

Figure 4A:
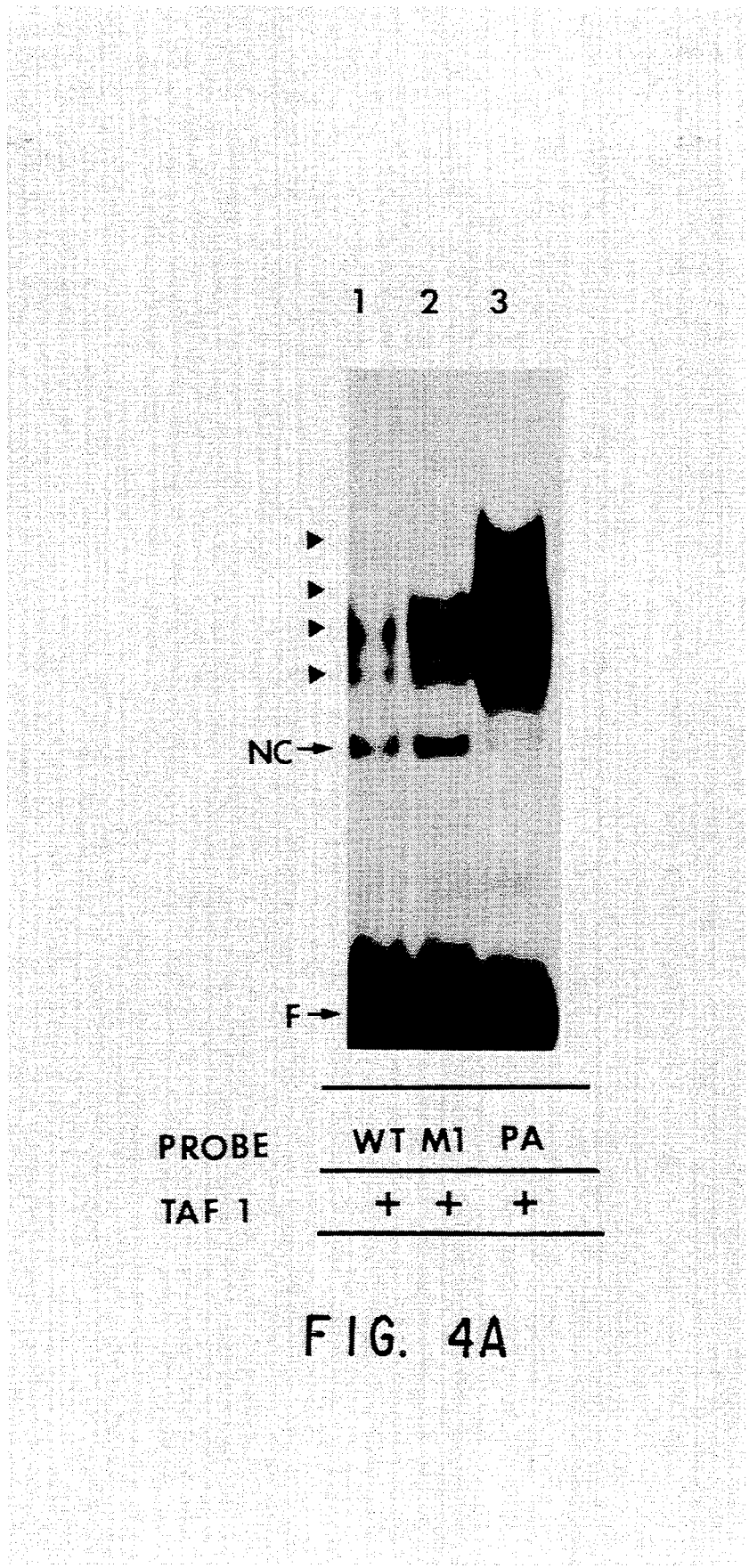
Figure 4B:
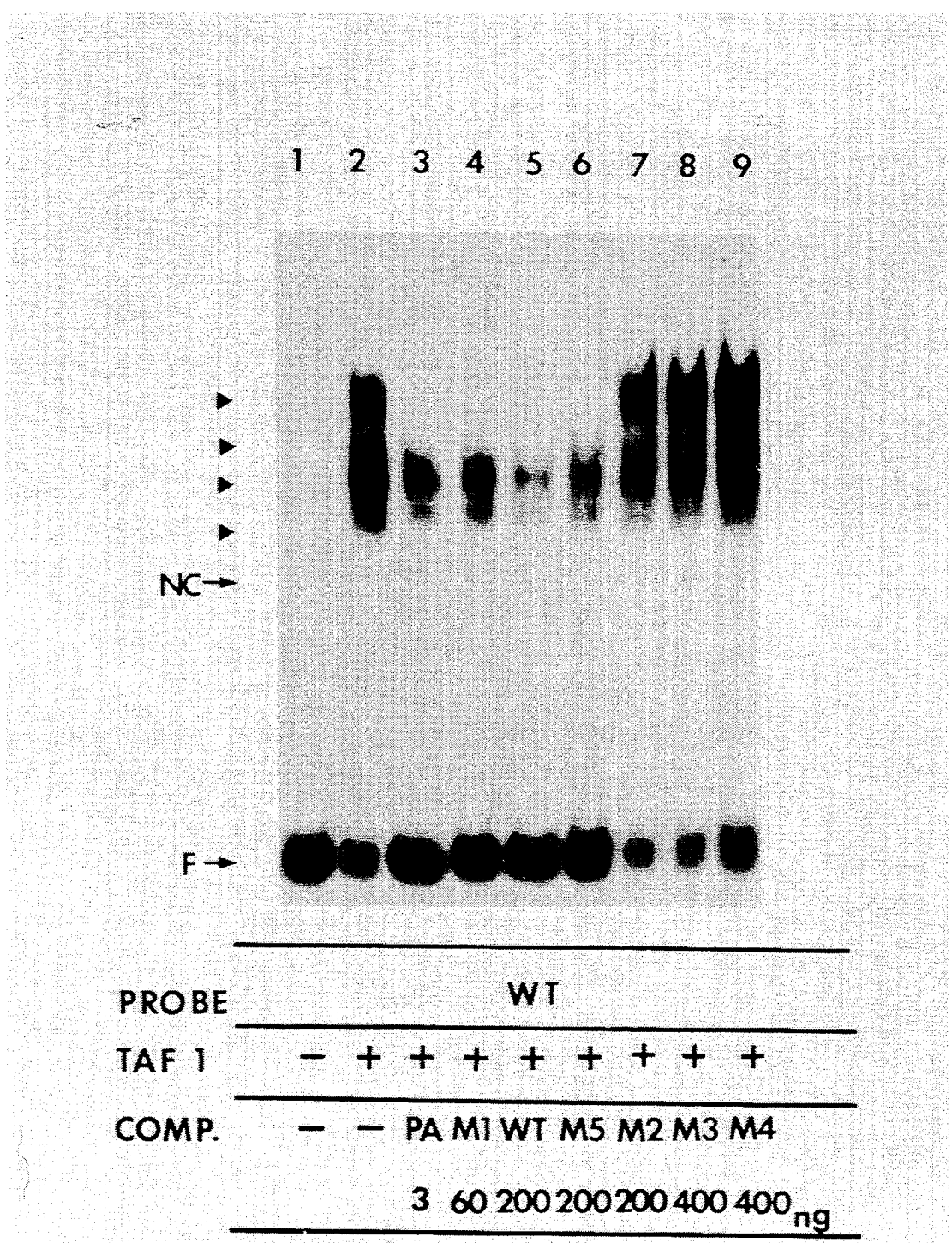
Figure 4D:
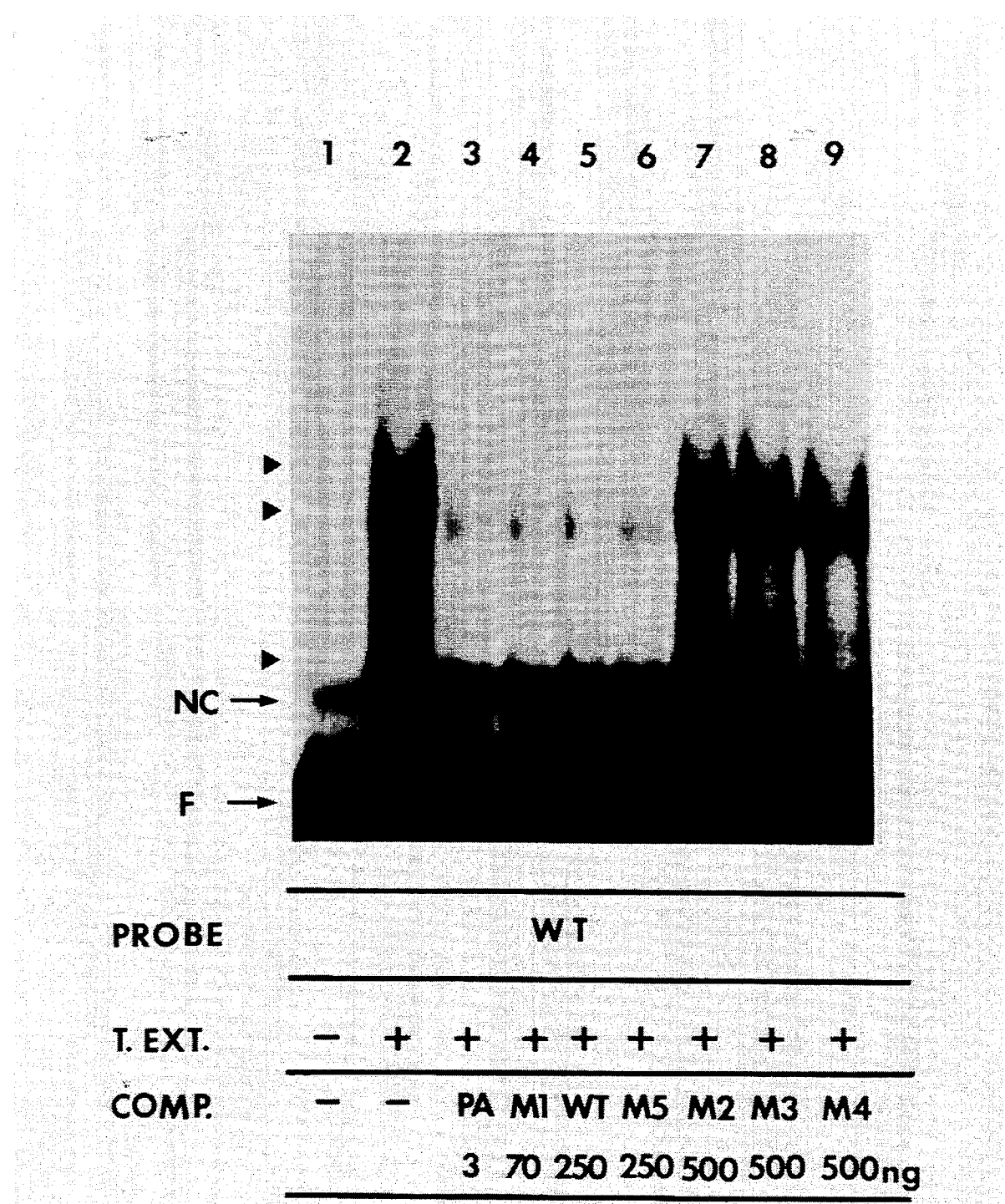

FIGS. 4A–4D. DNA-binding site sequence specifities of truncated TAF-1 and the nuclear motif I factor. FIG. 4A. TAF-1 preferentially binds to a perfect palindromic sequence. Tetramers of WT motif I, the mutant M1, and the perfect palindrome (PA), GCCACGTGGC, (SEQ. ID NO: 9) were used as probes in gel mobility shift-assays with E. coli extracts containing the truncated TAF-1. F, free probe; NC, non-specific complex. The specific complexes, indicated with arrowheads, have a slower mobility as compared to the non-specific complex. FIG. 4B. Relative binding affinities of TAF-1 to motif I (WT) and related sequences. WT motif I tetramer was used as a probe in gel mobility shift assays with E. coli extracts containing the truncated TAF-1. Different concentrations of tetramers of mutants M1 to M5, as well as the tetramer of the perfect palindromic sequence (PA) were tested for their ability to compete with the WT sequence for TAF-1. For WT, PA, M1 and M5, the concentrations that gave approximately 50% competition were used in the experiments shown here. Higher concentrations were used for mutants M2, M3 and M4. Comp., Competitor. FIG. 4C. Nucleotide sequences of WT (SEQ. ID NO: 11), mutants M1 to M5 (SEQ. ID NOS: 10, 13, 14, 15 and 12), and the perfect palindrome, PA (SEQ. ID NO: 9). In this figure, the WT motif I of the tetramer is shown with the TACGTG hexanucleotide as the core sequence. The 5' nucleotide G of the motif is derived from the 3' nucleotide of the preceding motif in the tetramer. Other sequences were represented accordingly. Nucleotide differences with PA are shown in lower cases. Relative binding affinities to TAF-1 are indicated on the right. FIG. 4D. Relative binding affinities of the nuclear motif I factor to motif I (WT) and related sequences. Experiments were carried out as in FIG. 4B. except that tobacco nuclear extracts (T. Ext.) were used. Note the slight difference in the concentrations of competitors between FIG. 4B and FIG. 4D. F, free probe; NC, non-specific complex; arrowhead indicate specific complexes.

Figure 6:
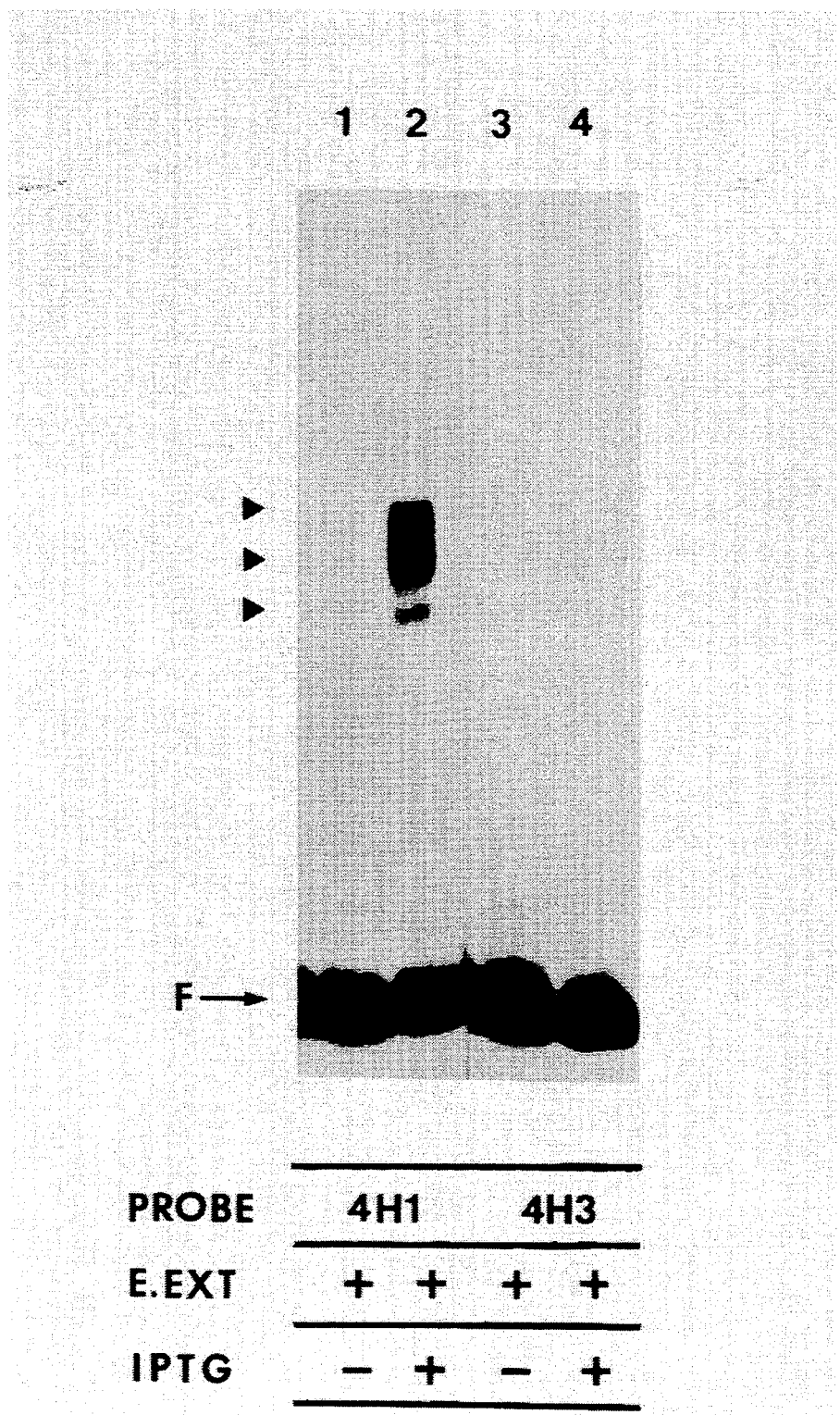

FIGS. 5A–5B. Comparison of amino acid sequences of the basic domains and the leucine repeats of plant bZip proteins. (A) Basic domains. TAF-1 (SEQ. ID NO: 16), EmBP-1 (SEQ. ID NO: 17), (Guiltinan et al., 1990, Science 250:267–271; HBP-1 (SEQ. ID NO: 18), Tabata et al., 1989 Science 245:965–967); OCSBF-1 (SEQ. ID NO: 19) (Singh et al., 1990, Plant Cell 2:891–903); O2 (SEQ. ID NO: 20) (Hastings et al., 1989, EMBO J. 8:2795–2801; Schmidt et al., 1990, Proc. Natl. Acad. Sci 87:46–50); TGA1A (SEQ. ID NO: 21) and TGA1B (SEQ. ID NO: 22) (Katagiri et al., 1989 Nature 340:727–730). Conserved amino acid residues are boxed. (B) Leucine repeats (SEQ. ID NOS: 23–26). For references, see FIGS. 5A. Repeated leucine residues are marked with asterisks. FIG. 6. TAF-1 binds to the hex motif of the wheat histone H3 promoter. E. coli extracts (E. ext) were prepared from IPTG-induced (+) and uninduced (−) cultures and fractionated with ammonium sulfate as detailed in the Materials and Methods. Gel mobility shift assays were performed using tetramers of the WT (4H1) or the mutant (4H3) hex sequence (Katagiri et al., 1989, Nature 340:727–730). WT, −180 TTCGGCCACGTCACCAATCCG −160 (SEQ. ID NO: 29); mutant, −180 TTCGGCCACGTCCAATCCG −160 (SEQ. ID NO: 30). Note that the three nucleotides at positions −168 to −170 have been changed to CGT from TCA. Specific complexes are indicated by arrows. F, free probe.

Figure 7:
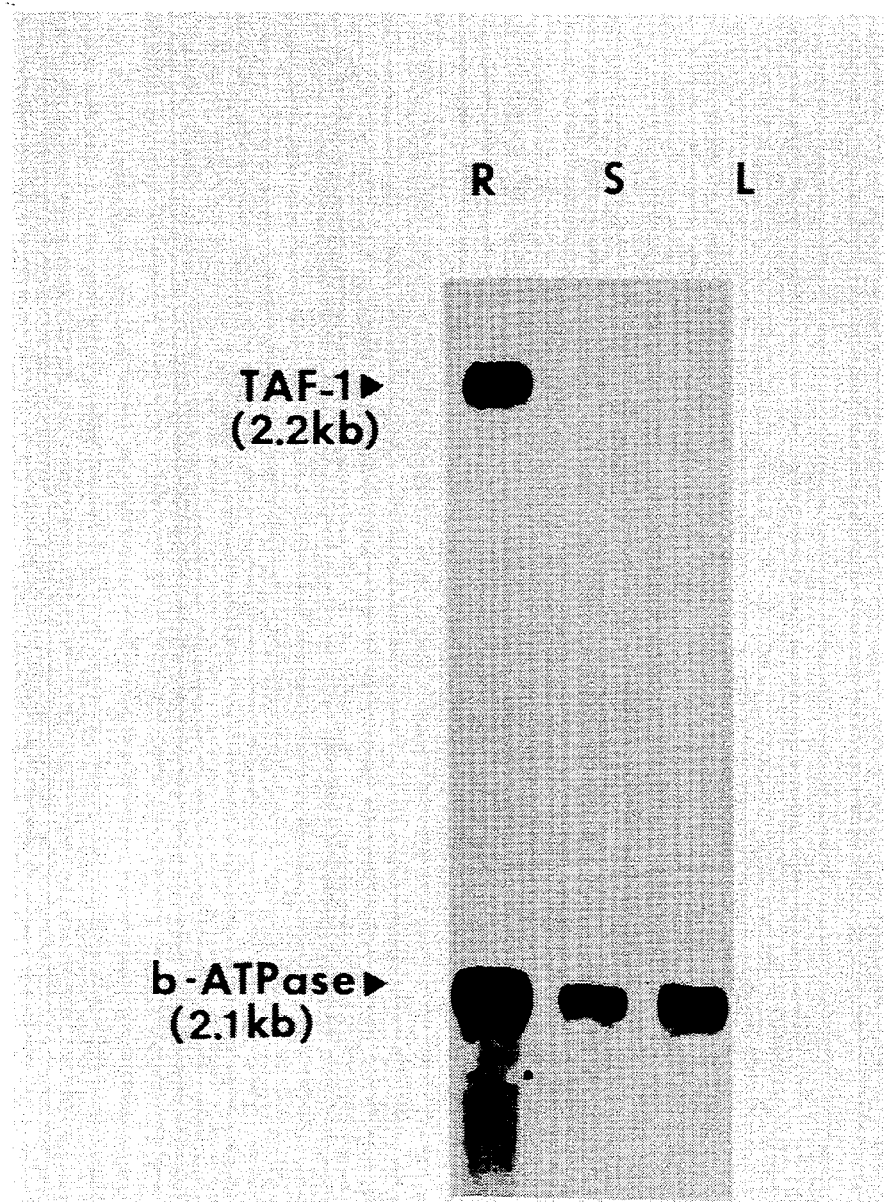

FIG. 7 Northern blot analysis of TAF-1 mRNA in different organs of the tobacco plant. Poly A RNA (1 μg) from root (R), stem (S), and leaf (L) of tobacco plants, were used. The hybridization probes were TAF-1 cDNA (upper panel) and β-ATPase cDNA (lower panel). For other details, see Materials and Methods.

5. DESCRIPTION OF THE INVENTION

The present invention relates to a novel transcription, TAF-1, which binds to certain motifs of promoter sequences. TAF-1 acts in trans to increase expression of gene sequences linked to binding sites for TAF-1. The structure, function and characterization of TAF-1 is described, as well as its use to increase gene expression in cell culture systems or transgenic plants.

The invention is illustrated by way of examples which demonstrate that tobacco nuclear extract contains a factor that binds to the rab16 motif I and that this binding is sensitive to competition by a G-Box motif. The motif I sequence (5′-GTACGTGGCG-3′) (SEQ. ID NO: 2) was utilized as a a probe to screen a tobacco expression library for expression products that bind to motif I. a partial cDNA clone called TAF-1 was isolated. This partial cDNA, TAF-1, encodes a truncated protein containing an acidic domain at its amino terminus, as well as a domain abutting a leucine repeat at the carboxy terminal portion of protein, characteristic of a "leucine zipper" protein. Both the nuclear factor and the truncated TAF-1 bind to motif I and the G-box motif.

To demonstrate that TAF-1 acts in trans to increase gene expression, various motif I type sequences were inserted into the CaMV 35S promoter and fused to the reporter gene, GUS. These chimeric fusions were stably transformed into tobacco via Agrobacterium mediated transformation. A CaMV 35S-TAF-1 fusion was constructed and plasmid DNA containing this fusion was introduced by high velocity bombardment into cells of transgenic leaves carrying the motif I teramer-GUS transgene constructions. Transient expression of the 35S-TAF-1 effector plasmid increased GUS expression 10 to 15 fold, over control cells of 2-fold. Therefore, the TAF-1 truncated, trans-acting factor binds motif I related sequences, causing activation of downstream heterologous structural genes.

The characteristics of TAF-1 are detailed in the subsections below, which describe (a) the structure and function of TAF-1 and its binding motifs; (b) production of TAF-1; and (c) the use of TAF-1 to increase gene expression in cell culture systems or in transgenic plants.

5.1 STRUCTURE OF TAF-1

Nucleotide sequence analysis of the partial cDNA clone p5a shows that the truncated TAF-1 ($Mr \approx 26,000$) contains at its carboxy terminus a basic domain abutting a leucine repeat (FIG. 2) (SEQ. ID NO: 1). This bipartite structure is characteristic of the bZip class of DNA-binding proteins (Vinson et al., 1989, Science 246:911–916). So far, cDNA clones encoding five other plant bZip proteins have been isolated and characterized (Katagiri et al., 1989, Nature 340:727–730; Tabata et al., 1989, Science 245:965–967; Hasting et al., 1989, EMBO J. 8:2795–2801; Schmidt et al., 1990, Proc. Natl. Acad. Sci. USA 87:46–50; Singh et al., 1990, Plant Cell 2:891–903). Guiltinan et al., (1990, Science 250:267–271) described a partial cDNA clone encoding a wheat bZip protein that binds to a conserved sequence within a 75-bp ABA responsive element. Amino acid sequence comparison between TAF-1 (SEQ. ID NO: 16) and these six other bZip proteins (SEQ. ID NOS: 17–22) shows a high degree of homology only in the basic domain (FIG. 5A). The most striking conservation is found among TAF-1 (SEQ. ID NO: 16), HBP-1 (SEQ. ID NO: 18). (Tabata et al., 1989, Science 245:965–967), EmBP-1 (SEQ. ID NO: 17) (Guiltinan et al., 1990 Science 250:267–271), and OCSBF-1 (SEQ. ID NO: 19) (Singh et al., 1990, Plant Cell 2:891–903). The basic domains of TAF-1 and EmBP-1 are virtually identical, with a single substitution of Lys for Arg at position 4. Since the basic domain of bZip proteins is involved in DNA recognition, this sequence conversation implies that the target DNA sequences of these DNA-binding proteins are likely to be similar. Table I, infra, shows that this is indeed the case for TAF-1, HBP-1, and EmBP-1.

The sequence homology between TAF-1 (SEQ. ID NO: 23) and EmBP-1 (SEQ. ID NO: 24) also extends in part, to the leucine zipper region (FIG. 5B), raising the possibility that these two proteins may interact to form heterodimers.

5.2 FUNCTION OF TAF-1

As demonstrated in the working examples, described infra, tobacco nuclear extract contains a factor that interacts specifically with the motif I sequence conserved in rab (Mundy and Chua, 1988, EMBO J. 7:2279–2286; Yamaguchi-Shinozaki et al., 1990, Plant Mol. Biol. 14:29–39) and lea (Baker et al., 1988, Plant Mol. Biol. 11:277–291) genes. From a tobacco cDNA expression library we have isolated a partial cDNA clone, p5a (SEQ. ID NO: 1), encoding a C-terminal portion of a protein designated as TAF-1. The truncated TAF-1 protein produced in E. coli has binding specificities very similar, if not identical, to the nuclear motif I factor when tested with a panel of discriminating probes (cf. FIGS. 4B and D). This result provides strong evidence that the full-length TAF-1 is the nuclear motif I factor or, accounts for a part of its activity.

5.2.1. TAF-1 CAN FUNCTION AS A TRANS-ACTIVATOR

Of the six plant bZip proteins described thus far, only two of them have been implicated in regulating transcription. There is genetic data demonstrating a requirement of the O2 gene product for the transcription of the 22 Kd zein gene (Jones et al., 1977, Plant Physiol. 59:525–529). Based on this genetic evidence, O2 is likely to be a positive regulator. Recent biochemical evidence indicates that the tobacco bZip protein, TGA1a functions as an activator in a plant (Yamazaki et al., 1990, Proc. Natl. Acad. Sci. USA 87:7035–7039) as well as a HeLa in vitro transcription system (Katagiri et al., 1990, Genes and Development 4:1899–1909). Furthermore, purified TGA1a protein can activate transcription of the −90 CaMV 35S/GUS chimeric gene (Benfey et al., 1989, EMBO J.8:2195–2202) when microinjected into leaf cells of transgenic tobacco harboring this reporter construct. This result indicates that TGA1a can also function as a transcription activator in vivo. A major point of the experiments described in the examples herein is the demonstration that TAF-1 is not only a DNA-binding protein, but also a transcriptional activator. The example demonstrate that a 35S truncated TAF-1 chimeric gene, when expressed transiently in tobacco leaf cells, can increase the expression of a GUS reporter gene linked to the wild type motif I tretramer, but not a mutant tetramet. These results demonstrate that TAF-1 can function as a transactivator in vivo. In this connection, it should be noted that the amino terminal region (amino acids 1 to 86) (SEQ. ID NO: 1) of the truncated TAF-1 is acidic and therefore, may serve as a transcription activation domain (cf. Johnson and McKnight, 1989, Ann. Rev. Biochem. 58:799–839).

5.2.2. RELATIONSHIP OF TAF-1 TO GBF AND CG-1

Although TAF-1 was originally isolated as a DNA-binding protein specific for motif I of rab genes, it binds with higher affinity to the perfect palindromic sequence GCCACGTGGC (FIG. 4) (SEQ. ID NO: 9) which contains the hexanucleotide core CACGTG found in G-box and related motifs of several plant promoters (Table I). The palindromic sequence is identical to the G-box sequence for petunia rbcS-611 gene (Turner et al., 1986, Nuc. Acad. Res. 14:3325–3342) and differs from the Arabidopsis rbcS-1A G-box by only 1-bp (Table I). This result suggests that TAF-1 can also recognize other G-box sequences and related motifs.

TABLE I

Recognition Sequences of Several Plant DNA-Binding Proteins

| DNA-Binding Protein | Recognition Sequence | Position | Gene |
|---|---|---|---|
| GBF | GCCACGTGTC | −253 | tomato rbcS-3A a/ (SEQ. ID NO: 31) |
| | TCCACGTGGC | −236 | A. thaliana rbcS-1A (SEQ. ID NO: 32) |
| | TACACGTGGC | −228 | pea rbcS-3.6 (SEQ. ID NO: 33) |
| | CAGACGTGGC | −240 | N. plumbaginifolia CAB-E b/ (SEQ. ID NO: 34) |
| | GCCACGTGGA | −213 | A. thaliana Adh c/ (SEQ. ID NO: 35) |
| CG-1 | GTCACGTGCC | −122 | A. majus chs d/ (SEQ. ID NO: 36) |
| | TCCACGTGGC | −155 | P. crispum chs (SEQ. ID NO: 37) |
| | TACACGTGGC | −277 | N. tabacum rbcS (SEQ. ID NO: 38) |
| | GCCACGTGAC | −57 | Adenovirus major late promoter (SEQ. ID NO: 39) |
| HBP-1 | GTGACGTGGC | −171 | wheat histone H3* gene e/ (SEQ. ID NO: 40) |
| EmBP-1 | GACACGTGGC | −147 | wheat EM f/ (SEQ. ID NO: 41) |
| | GTGACGTGGC | −171 | wheat histone H3* gene (SEQ. ID NO: 40) |
| OCSBF-1 | -TGACGTAA- | | OCS element concensus g/ |
| TAF-1 | GGTACGTGGC | | rice rab A–D (SEQ. ID NO: 42) |
| | GCCACGTGGC | −190 | Petunia rbcS-611 (SEQ. ID NO: 43) |
| | GTGACGTGGC | −171 | wheat histone H3* gene (SEQ. ID NO: 40) |

*Sequence of the bottom strand DNA was shown.
a/ Giulianio et al., 1988, Proc. Natl. Acad. Sci. USA 85:7089–7093.
b/ Schindler & Cashmore, 1990, EMBO J. 9:3415–3427.
c/ McKendree et al., 1990, Plant Cell 2:207–214.
d/ Staiger et al., 1989, Proc. Natl. Acad. Sci. USA 86:6930–6934.
e/ Tabata et al., 1989, Science 245:965–967.
f/ Guiltinan et al., 1990, Science 250:267–271.
g/ Singh et al., 1990, Plant Cell 2:891–903.

Plant nuclear factors that recognize G-box and related motifs in vitro have been reported by several laboratories (Table I). The GBF of tomato and Arabidopsis binds to the G-box of tomato rbcS-3A, Arabidopsis rbcS-1A, pea rbcS-3.6 (Giuliano et al., 1988, supra), and a similar motif, CAGACGTGGC (SEQ. ID NO: 34)., located at −240 of the N. plumbaginifolia Cab-E promoter (Schindler and Cashmore, 1990, supra; Table II). Whole cell extracts of Arabidopsis cell cultures also contain GBF activity (McKendree et al., 1990, supra), which binds to the G-box elements of rbcS-1A and Adh, but not to the related motif, GCCACGTGAC (SEQ. ID NO: 39), found in the upstream activating element (UAE) of the adenovirus major later promoter (Table I). In tobacco and other higher plants, Staiger et al., (1989, Proc. Natl. Acad. Sci. 86:6930–6934) have described a nuclear factor CG-1 that interacts with the G-box like motif located in the upstream region of A. majus (SEQ. ID NO: 361 and P. crispum (SEQ. ID NO: 37) chs genes. CG-1 may be distinct from GBF because it binds to the UAE of the adenovirus major late promoter but not the N. plumbaginifolia Cab-E promoter (SEQ. ID NO: 34) (Table I). Taken together, the in vitro binding experiments using plant nuclear extracts are consistent with multiple G-box-binding factors that possess overlapping specificities.

The notion of a family of G-box-binding proteins in plants is supported by three additional lines of evidence. First, the GBF in Arabidopsis leaf nuclear extracts forms at least two complexes with G-box sequences (Giuliano et al., 1988, Proc. Natl. Acad. Sci. 85:7089–7093) which differ in mobility from that formed by the GBF of Arabidopsis cell culture (McKendree et al., 1990, Plant Cell 2:207-214). This result indicates that Arabidopsis may contain more than one GBF. Indeed, UV cross-linking experiments have shown that the Arabidopsis GBF activity can be attributed to at least two proteins of $Mr \approx 18{,}000$ and $31{,}000$ (DeLisle and Ferl, 1990, Plant Cell 2:547-557). Second, the results obtained with recombinant DNA-binding proteins so far demonstrate that at least two different factors, TAF-1 and the recently described EmBP-1 (Guiltinan et al., 1990), can bind to G-box-related sequences (SEQ. ID NO: 41 and 40) (Table I). In view of the conserved amino acid sequences in their basic domains (FIG. 5A), we predict that HBP-1 (SEQ. ID NO: 25) and OCSBF-1 (SEQ. ID NO: 26) would also bind to the G-box and related motifs as well. This possibility should be tested by future experiments. Third, nuclear extracts of cauliflower contain at least three factors that recognize the CACGTG core motif but differ in their preferences for flanking sequences.

It is particularly important to point out that both TAF-1 and EmBP-1 bind to the hex motif, GTGACGTGGC (SEQ. ID NO: 45)., of the wheat histone H3 gene, which deviates from the perfect palindromic sequence by only 2-bp (Table I). At least three other proteins, the tobacco TGA1a (SEQ. ID NO: 21[and TGA1b (SEQ. ID NO: 22) (Katagiri et al., 1989) and the wheat HBP-1 (SEQ. ID NO: 40) (Tabata et al., 1989) can recognize the same hex sequence. Whether these three proteins would also interact with the G-box remains to be established.

The perfect palindromic sequence (PA), GCCACGTGGC (SEQ. ID NO: 9), differs by only 1-bp from the sequence of the upstream activating element (UAE), GCCACGTGAC (SEQ. ID NO: 39), located at −62 to −53 of the adenovirus major late promoter. The UAE can interact with two human transcription factors, USF and TFE-3, and full length cDNA clones encoding these factors have been reported recently (Gregor et al., 1990, Genes and Dev. 4:1730-1740; Beckmann et al., 1990, Genes and Dev. 4:167-179). In contrast to TAF-1 which is a bZip protein, both USF and TFE-3 are c-myc related proteins containing a helix-loop-helix (HLH) motif preceded by a basic domain that is presumably involved in DNA recognition. Notwithstanding the striking similarity in the nucleotide sequence of their recognition sites, there is no obvious homology in the amino acid sequence of the basic domains between TAF-1 and these two human transcription factors.

5.2.3. FUNCTION OF TAF-1 IN VIVO

Although truncated TAF-1 can function as a transcriptional activator, nuclear genes controlled by this regulatory protein remain to be identified. The abundance of TAF-1 mRNA in roots suggests that this factor may regulate genes that are preferentially expressed in roots, e.g., alcohol dehydrogenase gene (DeLisle and Ferl, 1990, Plant Cell 2:547-557). The role of TAF-1 in leaf tissue is less clear. This factor can potentially interact with the G-box motif located upstream of rbcS and Cab genes (cf. Gilmartin et al., 1990, Plant Cell 2:369-378; Schindler and Cashmore, 1990, EMBO J.9:3415-3427). Because a motif I tetramet gives little or no expression in leaf, it appears unlikely that its cognate factor can function independently. On the other hand, a higher affinity binding site, e.g. PA, may overcome the problem of low factor abundance and confer leaf expression. The favored hypothesis is that TAF-1 interacts with other factors to regulate the transcription of rbcS and Cab, and that this synergistic interaction is essential for high level expression of these photosynthetic genes in leaf. This may explain why mutation of the G-box motif reduces drastically the expression level of Arabidopsis rbcS-1A in transgenic tobacco plants (Donald and Cashmore, 1990, EMBO J.9:1717-1726). A similar situation may also apply to the P. crispum chs genes (Schulze-Lefert et al., 1989, EMBO J. 8:651-656; 1989b, Plant Cell 1:707-714), where there is in vivo evidence of a requirement of the G-box binding protein in UV-inducible expression.

Recently, Guiltinan et al., (1990, Science 250:267-271) reported that a 75-bp fragment of the wheat Em gene can give ABA-responsive transcription in transient assays using rice protoplasts. This fragment contains two conserved G-box-like motifs, Em1a GGACACGTGGC (SEQ. ID NO: 44) and Em1b GCACACGTGCC (SEQ. ID NO: 45), both of which have the CACGTG core sequence. Mutation of Em1a motif reduced the ABA induction ratio from 11 to 2 indicating that Em1a is necessary for the hormone induction. It is not known, however, whether Em1a alone can mediate ABA-responsive transcription or whether it has to interact with other cis-elements within the 75-bp fragment for this activity. Guiltinan et al., (1990, Science 250:267-271) 250:267-271) isolated a wheat partial cDNA clone encoding a DNA-binding protein, designated EmBP-1, that binds to the Em1a motif, as well as the hex element of wheat histone H3 promoter. In the case of tobacco, we found that TAF-1 also binds to the hex element in addition to motif (FIG. 6). Neither motif I tetramer nor the hex tetramet can confer ABA-inducible expression on a GUS reporter gene in transgenic tobacco. By contrast, a hex mutant element that has greatly reduced affinity for TAF-1 (FIG. 6) can confer ABA-responsive transcription in transgenic tobacco. These results would indicate that, at least in tobacco, motif I and TAF-1 are not directly involved in ABA responsive gene expression. It is possible, however, that motif I may interact with different regulatory factors in rice as opposed to tobacco and functions as an ABRE in rice. Such differences between monocot and dicot transcription systems have been noted previously (Keith and Chua, EMBO J.5:2419-2425, 1986).

5.3. PRODUCTION OF TAF-1

5.3.1. THE TAF-1 CODING SEQUENCE

The nucleotide coding sequence and deduced amino acid sequence for TAF-1 are depicted in FIG. 2A (SEQ. ID NO: 1). This nucleotide sequence, or fragments or functional equivalents thereof, may be used to generate recombinant DNA molecules that direct the expression of the TAF-1 gene product, or functionally active peptides or functional equivalents thereof, in appropriate host cells.

Due to the degeneracy of the nucleotide coding sequences, other DNA sequences which encode substantially the same amino acid sequences as depicted in FIG. 2A (SEQ. ID NO: 1) may be used in the practice of the present invention for the cloning and expression of TAF-1. Such alterations include deletions, additions or substitutions of different nucleotide residues resulting in a sequence that encodes the same or a functionally equivalent gene product. The gene product may contain deletions, additions or substitutions of amino acid residues within the sequence, which result in a silent change thus producing a bioactive product. Such amino acid substitutions may be made on the basis of similarity in polarity, charge, solubility, hydrophobicity, hydrophilicity and/or the amphipathic nature of the residues involved. For example, negatively charged amino acids include aspattic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine.

The genomic sequences for TAF-1 may be obtained from any plant cell source, whereas mRNA for preparation of cDNA copies may be obtained from cell sources that produce TAF-1. For example, parts of plants (e.g., leaves, stems, roots, nodules, cotyledons, seeds, fruits, etc.) may be ground and used as the source for extracting DNA or RNA. Alternatively, plant cell lines can be used as a convenient source of DNA or RNA.

The TAF-1 coding sequence may be obtained by cDNA cloning of RNA isolated and purified from such cellular sources or by genomic cloning. Either cDNA or genomic libraries may be prepared from the DNA fragments generated using techniques well known in the art, including but not limited to the use of restriction enzymes. The fragments which encode TAF-1 may be identified by screening such libraries with a nucleotide probe that is substantially complementary to any portion of the sequences depicted in FIG. 2A (SEQ. ID NO: 1). To these ends, techniques well known to those skilled in the art for the isolation of DNA, generation of appropriate restriction fragments, construction of clones and libraries, and screening recombinants may be used. For a review of such techniques see, for example, Maniatis et al., 1982, Molecular Cloning A Laboratory Manual, Cold Spring Harbor Press, N.Y., Chapters 1–11. Oligonucleotide probes representing cis-acting elements acting in trans with the protein product of interest may be utilized to screen a cDNA expression library. Alternatively, oligonucleotides derived from the TAF-1 sequence could be used as heterologous primers in PCR (polymerase chain reactions) to generate cDNA or genomic copies of TAF-1 sequences from other species. For a review of such PCR techniques, see for example, Gelfand, D. H., 1989, "PCR Technology. Principles and Applications for DNA Amplification," Ed., H. A. Erlich, Stockton Press, N.Y.; and "Current-Protocols in Molecular Biology," Vol. 2, Ch. 15, Eds. Ausubel et al., John Wiley & Sons, 1988.

In an alternate embodiment of the invention, the coding sequence of FIG. 2A (SEQ. ID NO: 11 could be synthesized in whole or in part, using chemical methods well known in the art. See, for example, Caruthers, et al., 1980, Nuc. Acids Res. Symp. Ser. 7:215-233; Crea and Horn, 180, 180, Nuc. Acids Res. 9(10): 2331; Matteucci and Caruthers, 1980, Tetrahedron Letters 21:719; and Chow and Kempe, 1981, Nuc. Acids Res. 9(12) 2807-2817. Alternatively, the protein itself could be produced using chemical methods to synthesize the amino acid sequence depicted in FIG. 2A (SEQ. ID NO: 1) in whole or in part. For example, peptides can be synthesized by solid phase techniques, cleaved from the resin, and purified by preparative high performance liquid chromatography. (E.g., see, Creighton, 1983, Proteins Structures and Molecular Principles, W. H. Freeman and Co., N.Y. pp. 50-60). The composition of the synthetic peptides may be confirmed by amino acid analysis or sequencing (e.g., the Edman degradation procedure; see Creighton, 1983, Proteins Structures and Molecular Principles, W. H. Freeman and Co., N.Y. pp. 34-49).

5.3.2. CONSTRUCTION OF EXPRESSION VECTORS CONTAINING THE TAF-1 CODING SEQUENCE

In order to express a biologically active TAF-1 the nucleotide sequence coding for TAF-1, or a functional equivalent as described in Section 5.3.1, supra, a vector which contains the necessary elements for the transcription and translation of the inserted coding sequence. The TAF-1 gene product as well as host cells, cell lines or plants transfected or transformed with recombinant TAF-1 expression vectors can be used for a variety of purposes.

Methods which are well known to those skilled in the art can be used to construct expression vectors containing the TAF-1 coding sequence and appropriate transcriptional/translational control signals. These methods include in vitro recombinant DNA techniques, synthetic techniques and in vivo recombination/genetic recombination. See, for example, the techniques described in Maniatis et al., 1982 Molecular Cloning a Laboratory Manual, Cold Spring Harbor Laboratory, N.Y., Chapter 12.

A variety of host-expression vector systems may be utilized to express the TAF-1 coding sequence. These include but are not limited to microorganisms such as bacteria transformed with recombinant bacteriophage DNA, plasmid DNA or cosmid DNA expression vectors containing the TAF-1 coding sequence; yeast transformed with recombinant yeast expression vectors containing the TAF-1 coding sequence; insect cell systems infected with recombinant virus expression vectors (e.g., baculovirus) containing the TAF-1 coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the TAF-1 coding sequence; or animal cell systems infected with recombinant virus expression vectors (e.g., adenovirus, vaccinia virus) containing the plant TAF-1 coding sequence (See SEQ. ID NO: 1 for the nucleotide sequence encodinq TAF-1.).

The expression elements of these vectors vary in their strength and specificities. Depending on the host/vector system utilized, any of a number of suitable transcription and translation promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used. Promoters produced by recombinant DNA or synthetic techniques may also be used to provide for transcription of the inserted TAF-1 coding sequence.

In bacterial systems a number of expression vectors may be advantageously selected depending upon the use intended for the TAF-1 expressed. For example, when large quantities of TAF-1 are to be produced for the generation of antibodies, vectors which direct the expression of high levels of fusion protein products that are readily purified may be desirable. Such vectors include but are not limited to the *E. coli* expression vector pUR278 (Ruther et al., 1983, EMBO J. 2:1791), in which the TAF-1 coding sequence may be ligated into the vector in frame with the lac Z coding region so that a hybrid TAF-1-lac Z protein is produced; pIN vectors (Inouye & Inouye, 1985, Nucleic acids Res. 13:3101–3109; Van Heeke & Schuster, 1989, J. Biol. Chem. 264:5503–5509); and the like. However, where the expression of unfused TAF-1 is desired, expression vectors with few or no host genotype requirements, including, but not limited to vectors such as ptac12, (Amann et al., 1983, Gene 25:167) and the like may be preferred.

In yeast, a number of vectors containing constitutive or inducible promoters may be used. For a review see, Current Protocols in Molecular Biology, Vol. 2, 19833, Ed. Ausubel et al., Green Publish. Assoc. & Wiley Interscience, Ch. 13; Grant et al., 1987, Expression and Secretion Vectors for Yeast, in Methods in Enzymology, Eds. Wu & Grossman, 31987, Acad. Press, N.Y., Vol. 153, pp. 516–544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673–684; and The Molecular Biology of the Yeast Saccharomyces, 1982, Eds. Strathen et al., Cold Spring Harbor Press, Vols. I and II.

In cases where plant expression vectors are used, the expression of the TAF-1 coding sequence may be driven by any of a number of promoters. For example, viral promoters such as the 35S RNA and 19S RNA promoters of CaMV (Brisson et al., 1984, Nature 310:511–514), or the coat protein promoter of TMV (Takamatsu et al., 1987, EMBO J. 6:307–311) may be used; alternatively, plant promoters such as the small subunit of RUBISCO (Coruzzi et al., 1984, EMBO J. 3:1671–1680; Broglie et al., 1984, Science 224:838–843); or heat shock promoters, e.g., soybean hsp17.5-E or hsp17.3-B (Gurley et al., 1986, Mol. Cell. Biol. 6:559–565) may be used. These constructs can be introduced into plant cells using Ti plasmids, Ri plasmids, plant virus vectors, direct DNA transformation, microinjection, electroporation, particle bombardment, etc. For reviews of such techniques see, for example, Weissbach & Weissbach, 1988, Methods for Plant Molecular Biology, Academic Press, NY, Section VIII, pp. 421–463; and Grierson & Corey, 1988, Plant Molecular Biology, 2d Ed., Blackie, London, Ch. 7–9.

As alternative expression system which could be used to express TAF-1 is an insect system. In one such system, *Autographa california* nuclear polyhidrosis virus (AcNPV) is used as a vector to express foreign genes. The virus grows in *Spodoptera frugiperda* cells. The TAF-1 coding sequence may be cloned into non-essential regions (for example the polyhedrin gene) of the virus and placed under control of an AcNPV promoter (for example the polyhedrin promoter). Successful insertion of the TAF-1 coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (E.g., see Smith et al., 1983, J. Viol. 46:584; Smith, U.S. Pat. No. 4,215,051).

In cases where an adenovirus is used as an expression vector, the TAF-1 coding sequence may be ligated to an adenovirus transcription/translation control complex, e.g., the late promoter and tripartite leader sequence. This chimeric gene may then be inserted in the adenovirus genome in in vitro or in vitro recombination. Insertion in a non-essential region of the viral genome (e.g., region E1 or E3) will result in a recombinant virus that is viable and capable of expressing TAF-1 in infected hosts. (E.g., See Logan & Shenk, 1984, Proc. Natl. Acad. Sci. (USA) 81:3655–3659). Alternatively, the vaccinia 7.5K promoter may be used. (E.g., see Mackett et al., 1982, Proc. Natl. Acad. Sci. (USA) 79:7415–7419; Mackett et al., 1984 J. Virol. 49:857–864; Panicali et al., 1982, Proc. Natl. Acad. Sci. 79:4927–4931).

Specific initiation signals may also be required for efficient translation of inserted TAF-1 coding sequences. These signals include the ATG initiation codon and adjacent sequences. In cases where the entire TAF-1 gene, including its own initiation codon and adjacent sequences, are inserted into the appropriate expression vectors, no additional translational control signals may be needed. However, in cases where only a portion of the TAF-1 coding sequence is inserted, exogenous translational control signals, including the ATG initiation codon, must be provided. Furthermore, the initiation codon must be in phase with the reading frame of the TAF-1 coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al., 1987, Methods in Enzymol. 153:516–544).

In addition, a host cell strain may be chosen which modulates the expression of the inserted sequences, or modifies and processes the gene product in the specific fashion desired. Expression driven by certain promoters can be elevated in the presence of certain inducers, (e.g., zinc and cadmium ions for metallothionein promoters). Therefore, expression of the genetically engineered TAF-1 may be controlled. This is important if the protein product of the cloned foreign gene is lethal to host cells. Furthermore, modifications (e.g., glycosylation) and processing (e.g., cleavage) of protein products may be important for the function of the protein. Different host cells have characteristic and specific mechanisms for the post-transnational processing and modification of proteins. Appropriate cells lines or host systems can be chosen to ensure the correct modification and processing of the foreign protein expressed.

5.3.3. IDENTIFICATION OF TRANSFECTANTS 0R TRANSFORMANTS EXPRESSING THE TAF-1 GENE PRODUCT AND ISOLATION OF TAF-1

The host cells which contain the TAF-1 coding sequence and which express the biologically active TAF-1 gene product may be identified by at least four general approaches: (a) DNA-DNA hybridization; (b)

the presence or absence of "marker" gene functions; (c) assessing the level of transcription as measured by the expression of TAF-1 mRNA transcripts in the host cell; and (d) detection of the TAF-1 gene product as measured by immunoassay or by its biological activity.

In the first approach, the presence of the plant TAF-1 coding sequence inserted in the expression vector can be detected by DNA-DNA hybridization using probes comprising nucleotide sequences that are homologous to the plant TAF-1 coding sequence substantially as shown in FIG. 2A (SEQ. ID NO: 1) or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the TAF-1 coding sequence is inserted within a marker gene sequence of the vector, recombinants containing the TAF-1 coding sequence can be identified by the absence of the marker gene function. Alternatively, a marker gene can be placed in tandem with the TAF-1 sequence under the control of the same or different promoter used to control the expression of the plant TAF-1 coding sequence. Expression of the marker in response to induction or selection indicates expression of the TAF-1 coding sequence. One such marker gene construct which is of particular value for monitoring promoter activity in plant cells and plants are the bacterial glucuronidase genes, GUS (Jefferson et al., 1987, EMBO J. 6:3901-3908).

In the third approach, transcriptional activity for the TAF-1 coding region can be assessed by hybridization assays. For example, RNA can be isolated and analyzed by Northern blot procedures using a probe homologous to the TAF-1 coding sequence or particular portions thereof substantially as shown in FIG. 2A (SEQ. ID NO: 1). Alternatively, total nucleic acids of the host cell may be extracted and assayed for hybridization to such probes.

In the fourth approach, the expression of the TAF-1 protein product can be assessed immunologically, for example by Western blots, immunoassay such as radioimmuno-precipitation, enzyme-linked immunoassay and the like. The ultimate test of the success of the expression system, however, involves the detection of the biologically active TAF-1 gene product. Where the host cell secretes the gene product, the cell free media obtained from the cultured transfectant host cell may be assayed for TAF-1 activity. Where the gene product is not secreted, cell lysates may be assayed for such activity. In either case, a number of assays can be used to detect TAF-1 activity, including but not limited to the partial purification of recombinant TAF-1 with the appropriately labeled and unlabeled DNA fragments.

5.4 USE OF TAF-1 TO INCREASE GENE EXPRESSION

TAF-1 may be utilized to stimulate transcription of a gene controlled by a promoter containing cis-acting elements that bind TAF-1 in either plant cell culture systems or in transgenic plants. Although exogenous TAF-1 (produced in accordance with Section 5.3, supra) could be added to such systems, in a preferred embodiment, the TAF-1 gene expression constructs (such as the constructs described supra) could be engineered into the cell culture system or a transgenic plant in addition to the gene of interest controlled by a promoter containing a TAF-1 binding motif. Induction of expression of TAF-1 will increase expression of the gene of interest in the cell culture system including but not limited to yeast, plant or animal cell cultures, or transgenic plants.

A number of combinations in which the binary expression system driven by TAF-1 would be functional may be designed. For example, both fusion constructions might well be placed in tandem within the same DNA vector. Alternatively, the respective constructs may be placed in separate DNA vectors, possibly with distinct selectable marker genes. Within this array of combinations, both heterologous constructs could be driven by the same or different promoter system (see section 5.3.2, supra, for a discussion of various promoter systems). The heterologous promoter element activated by TAF-1 could possess one or more copies of the cis-acting element known to bind TAF-1. Numerous techniques available to the skilled artisan would allow transformation of plant cells for use in plant cell culture or the regeneration of transgenic plants. Both constructions may be transformed simultaneously into the plant species of interest or cells from a stably transformed line containing one of the transgene constructions would be the target for a second transformation event. Several methods of plant transformation are available as described, infra.

This binary gene expression system should be functional in other eukaryotic as well as prokaryotic systems. For example, the TAF-1 truncated coding region as well as in the gene to be modulated or controlled may be fused to promoters contained within yeast expression plasmids or yeast integrating plasmids. These constructions could be transformed into an appropriate *Saccharomyces cerevisiae* host. The resultant transformant could be grown in culture to express the gene of interest. This example extends to include but not be limited to other eukaryotic expression systems as well as expression in prokaryotic organisms such as *E. coli* and *B. subtilus*.

In certain embodiments of the invention, the *Agrobacterium tumefaciens* gene transfer system may be used to introduce such recombinant constructs of the invention into plants; generally, this system may be utilized to transfer DNA into dicotyledonous plants (Bevan et al., 1982, Ann. Rev. Genet. 16:357-384; Rogers et al., 1986, Methods Enzymol. 118:627-641; Fraley et al., 1986, CRC Crit. Rev. Plant Sci. 4:1-46; Hooykaas et al., 1984, Adv. Genet. 22:210-283; Nester, et al., 1984, Ann. Rev. Plant. Physiol. 35:387-413). To this purpose, vectors such as, but not limited to, binary Agrobacterium vectors for plant transformation may be utilized, such as, for example, the vector described by Bevan (1984, Nucl. Acids Res. 12:8711-8721). Nicotiani tobacum xanthi may be transformed by a leaf inoculation procedure such as that described by Horsch et al. (1985, Science 227:12229-1231).

Additional methods for introducing DNA into plants may also be utilized, particularly if the recombinant construct is to be used to create a transgenic monocotyledonous plant. Such methods would include, but are not limited to, poly(ethylene glycol) and calcium-mediated uptake of naked DNA (Hain et al., 1985, Mol. Gen. Genet. 199:161-168; Paszkowski et al., 1984, EMBO J. 3:2717-2722; Potrykus et al., 1985, Mol. Gen. Genet. 199:169-177), electroporation (Fromm et al., 1985, Proc. Natl. Acad. Sci. U.S.A. 82:5824–5828) microinjection and the particle acceleration gun.

It may be desirable to transform host cells with an additional construct which contains a selectable marker or reporter gene in order to identify successful transformants. The additional construct may be introduced separately or in tandem with the construct which contains either the gene of interest or TAF-1. If not constructed in tandem, the additional construct may utilize the same promoter system, such that expression of the selectable marker or reporter gene function may serve as an indicator of promoter activity and thereby provide evidence that the gene of interest or the TAF-1 coding sequence is actively transcribed. Selectable markers may include genes which engender antibiotic resistance (for example, kanamycin resistance) or which encode a reporter gene, including, but not limited to, the chloramphenicol acetyl-transferase (CAT) gene used in the example described infra, the gene for β-glucuronidase (Jefferson, 1987, Plant. Mol. Bio. Rep. 5:387–405), neomycin phosphotransferase (NPT II), and luciferase (Ow et al., 1986, Science 234:856–859) to name but a few. Detection of reporter gene expression may then be performed using methods known in the art.

Alternatively, transformants may be tested for the presence of recombinant construct by methods which would identify foreign DNA sequences, such as the Southern blot procedure. Transcription of recombinant constructs could be detected by isolating DNA from the transformant and screening for the expected transcript by Northern blot or RNA protection. Likewise, translation of the desired protein could be detected by protein gel electrophoresis, Western blot techniques, immunoprecipitation or enzyme-linked immunoassay.

Using similar techniques, the expression of the recombinant constructs of the invention may be detected in specific plant organs or tissues by determining the presence of RNA, protein, selectable marker, or reporter gene which may serve as an indicator of transcription of the gene of interest or the TAF-1 coding sequence.

The examples, infra, illustrate the effects of TAF-1 using the reporter gene, GUS, fused downstream from the −90 promoter of CaMV 35S containing one to several copies of motif I-like sequence. This 35S-GUS transgene normally exhibits low level expression in leaf tissue. However, when a 35S-TAF-1 construction is transiently expressed in the transgenic leaf cell, a concomitant increase in expression of 35S-GUS is recorded. Although particle bombardment was used to deliver the 35S-TAF-1 plasmid to the leaf cell, the invention is not so limited. Both constructions (i.e., the gene of interest controlled by a promoter sequence and the TAF-1 coding sequence controlled by a promoter sequence) may be stably transformed in the species of interest, with subsequent transgenic plants utilized without further genetic manipulation. Various other combinations of transient expression, stable transformation, modes of transformation, etc., in order to effect this dual system of increasing heterologous gene expression are feasible and would be evident to one of ordinary skill in the art.

6. EXAMPLE: CHARACTERIZATION OF TAF-1

Tobacco nuclear extract contains a factor that binds specifically to the motif I sequence (5′GTACGTGGCG 3′) (SEQ. ID NO: 2) conserved among rice rab genes and cotton lea genes (Yamaguchi-Sinozaki et al., 1990, Plant Mol. Biol. 14:29–39). In the subsections described below a partial cDNA clone encoding a truncated derivative of a protein designated as TAF-1 was isolated from a tobacco cDNA expression library. The truncated TAF-1 (Mr=26,000) contains an acidic region at its N-terminus and a bZip motif at its C-terminus. Using a panel of motif I mutants as probes, we showed that the truncated TAF-1 and the tobacco nuclear factor for motif I have similar, if not identical, binding specificities. In particular, both show high-affinity binding to the perfect palindrome 5′GCCACGTGGC 3′(SEQ. ID NO: 9), which is also known as the G-box motif (Giuliano et al., 1988, Proc. Natl. Acad. Sci. USA 85:7089–7093). TAF-1 mRNA is highly expressed in root, but the level is at least ten times lower in stem and leaf. Consistent with this observation, it was found that a motif I tetramer, when fused to the −90 derivative of the CaMV 35S promoter, is inactive in leaf of transgenic tobacco. The activity, however, can be elevated by transient expression of the truncated TAF-1. These results demonstrate that TAF-1 can bind to the G-box and related motifs and that it functions as a transcription activator.

6.1. MATERIALS AND METHODS

6.1.1. ISOLATION OF TAF-1 RECOMBINANT PHAGE

A random-primed cDNA library was constructed in λ zap vectors using polyA RNA prepared from tobacco seedlings (Nicotiana tabacum cv. SR1) adapted in the dark for two days. The amplified library was screened with a labeled oligonucleotide fragment that spans between −275 and −206 of rab16B (FIG. 1A), using essentially the screening protocal of Singh et al., (1988, Cell 52:415–423) with minor modifications by Katagiri et al., (1989, Nature 340:727–730).

6.1.2. NUCLEOTIDE SEQUENCE ANALYSES

Single-stranded templates were prepared from E. coli HB101 after infection with phage IR408 (Russel et al., 1986, Gene 45:333–338). Nucleotide sequences of both strands were determined by a Sequenase TM sequencing kit (USB) using common primers and synthesized primers. Sequence data were analyzed by DNASIS and PROSIS programs (Hitachi) on an IBMPS12 computer.

6.1.3. GEL MOBILITY-SHIFT ASSAYS

Gel mobility-shift assays were performed according to Green et al., (1987, EMBO J. 6:2543–2549). The assay mixture contained tobacco unclear extract (7.5 μg protein) or E. coli extract (5μg protein), 0.2 ng of binding probe (2×10⁴ cpm), and 5μg of poly (dI-dC) in 5 μl of B buffer (20 Mm HEPES-KOH, Ph 7.5), 40 Mm KCI, 1 Mm EDTA, 10% glycerol, and 0.5 Mm DTT. Tobacco nuclear extract was prepared as described (Green et al., 1987, supra). E. coli cells containing recombinant plasmids were grown to early log phase and incubated with 2 mM IPTG for 4 hours. Cells were collected and resuspended in buffer A (50 mM Tris-HCl, pH 7.5, 20% glycerol, 1 mM EDTA, and 5 mM DTT). The suspension was sonicated and the homogenate centrifuged at 10,000 ×g for 15 minutes. The supernatant fraction was divided into aliquots, frozen in liquid nitrogen and stored at −80° C. Oligonucleotides were synthesized on Applied Biosystems Model 380A DNA synthesizer. Full length products were purified on denaturing polyacrylamide gels, annealed and cloned into the HindIII/XhoI site of a pEMBL12-

+derivative (Dante et al., 1983, Nucleic Acid Research 11:1645-1655). Plasmid DNA containing the oligonucleotide insert was digested with HindIII and XhoI and labeled by fill-in reaction. The labeled insert was purified by polyacrylamide gel electrophoresis and used as binding probes.

6.1.4. PARTIAL PURIFICATION OF RECOMBINANT TAF-1

To 10 ml of *E. coli* extract prepared as described above, 2.43 g of ammonium sulfate was gradually added over 30 minutes to obtain 40% saturation. Protein precipitate was collected by centrifugation at 15,000 $\times$g for 30 minutes and resuspended in 1.25 ml of buffer A and dialyzed against buffer A containing 20 mM NaCl for 4 hours with three changes of 200 ml each. After dialysis, the extract was centrifuged in a microfuge for 10 minutes to remove insoluble materials. The supernatant fraction was divided into aliquots which were frozen in liquid nitrogen and stored at $-80°$ C.

6.1.5. NORTHERN AND SOUTHERN ANALYSIS

PolyA RNA was prepared (Katagiri et al., 1989, Genes and Development 4:1899-1909; Nagy et al., 1988, In Plant Molecular Biology Manual, eds. Gelvin, S. V. and Schilperoort, R. A., Kluwer, Dordrecht, Vol. B4, pp. 1-29), separated in formaldehyde gels and blotted into Nitran filters. The filters were hybridized to the labeled EcoRI fragment (1.2. Kb) of the cDNA clone 5a or the $\beta$-ATPase cDNA (Boutry and Chua, 1985, EMBO J. 4:2159-2165) in a solution containing 6$\times$SSC, sonicated salmon testis DNA, 0.5% SDS, 0.2% Ficoll at 37° C. for 24 hours. Filters were washed in 0.1$\times$SSC at 65° C. and autoradiographed. High molecular weight DNA was isolated from tobacco leaf (Ausubel et al., 1987, Current Protocols in Molecular Biology, Wiley, New York), and Southern blot analysis was performed as described by Maniatis et al., 1982, Molecular Cloning: A Laboratory Manual, Cold Spring Harbor Laboratory, Cold Spring Harbor, New York.

6.1.6. PRODUCTION OF TRANSGENIC PLANTS

Tetramers of wild-type and mutant motif I (FIG. 1A) were placed upstream of the vectors X-GUS-90 (Benfey et al., 1989, EMBO J. 8:2195-2202). *Agrobacterium tumefaciens* (GV3111SE) cells harboring the recombinant plasmid vectors were used to inoculate leaf discs of *Nicotiana tabacum* cv. SR1 and regenerated shoots were selected on medium containing kanamycin (200 μg/ml) (Horsch et al., 1985, Science, 227:1229-1231). After rooting, transgenic plantlets were transferred to soil and grown to maturity in a greenhouse. R-0 plants were selfed and R-1 seeds and seedlings were used for experiments.

6.1.7. β-GLUCURONIDASE (GUS) ENZYME ASSAYS

GUS enzyme activities in tobacco extracts were determined essentially as described, (Jefferson, et al., 1987, EMBO J. 6:3901-3907). Fluorescence was measured with a Perkin-Elmer LS5 fluorimeter. A solution of 100 mN 4-methyl umbelliferone (MU) in 0.2M sodium carbonate was used to caliberate the fluorescence intensity. Histochemical staining of GUS activity was according to published protocols (Jefferson et al., 1987, supra; Benfey et al., 1989, EMBO J. 8:2195-2202).

6.1.8. HIGH VELOCITY MICROPROJECTILE BOMBARDMENT

Five μg plasmid DNA was coated onto tungsten powder and delivered to leaf sections by high velocity acceleration of the tungsten particles using a homemade instrument designed by Professor Konstantin Goulianos (Laboratory of Experimental Physics, The Rockefeller University). This instrument is based on the principle described by Klein et al., 1988, Bio/Technology 6:559-563; Klein et al., 1989, Proc. Natl. Acad. Sci. USA 86:6681-6685. After bombardment, the leaf sections were incubated in a moist chamber in the dark at room temperature for 12 hours before measurement of GUS activity.

6.2. RESULTS

6.2.1 A TOBACCO FACTOR BINDS TO THE CONSERVED MOTIF I

The upstream regions of rice rab16 genes (A,B,C, and D) contain a conserved sequence called motif I, GTACGTGGCG (SEQ. ID NO: 2), that serves as a binding site for rice nuclear proteins (Mundy J., et al., 1990, Proc. Natl. Acad. Sci. USA 87:406-410; Yamaguchi-Shinozaki et al., 1990, Plant Mol. Biol. 14:29-39). This motif is also found in the upstream regions of other ABA-responsive genes (see Skriven and Mundy, 1990, Plant Cell 2:503-512 for a review). In the case of rab16B, motif I is located within a 70-bp region that spans from $-275$ to $-206$ (FIG. 1A). When this 70-bp fragment was used as a probe in gel mobility-shift assays using nuclear extracts prepared from tobacco leaves, two complexes designated as I and II in the order of increasing mobility were seen (FIG. 1B). To see whether one of the complexes resulted from specific interaction with motif I, we synthesized tetramers of motif I and its mutant derivative (FIG. 1A) and used them as competitors in gel mobility-shift assays. FIG. 1B shows that the slower-migrating complex I, was sensitive to competition by the wild type but not the mutant tetramer. These results indicated that nuclear extracts of tobacco leaves contain a factor that specifically binds to the conserved motif I of rice rab16B.

6.2.2 ISOLATION OF A cDNA CLONE ENCODING A PROTEIN BINDING TO MOTIF I

A tobacco leaf cDNA expression library was screened using the 70-bp fragment of rab16B (FIG. 1A) as a probe. Positive clones are those which bind the motif I nucleotide probe (FIG. 1A) from the rab16 promoter. One positive clone, p5a, was obtained from screening of 500,000 recombinant phages. The cDNA insert of 5a was subcloned into SK(−) plasmid and the recombinant plasmid p5a was used for further experiments.

The entire nucleotide sequence (SEQ. ID NO: 1) of the cDNA insert was determined by the dideoxy method (FIG. 2). The insert contains a partial cDNA of [1,345-bp]1,338-bp encoding an open reading frame of 265 amino acids, starting with an alanine which we have tentatively designated as the first amino acid residue. Analysis of the deduced amino acid sequence (SEQ. ID NO: 1) showed that the encoded protein contains at its C-terminus, six leucine residues (Nos. 222,229, 236, 243,250, and 257) arranged as heptad repeats. In addition, a stretch of basic amino acids (residues 196 and 215) is located adjacent to the N-terminus of the leucine repeats. These two structural motifs, the basic domain and the leucine zipper, are characteristic features of a class of transcription factors referred to as the bZip proteins (Vinson et al., 1989, Science 246:911–916). It has been shown that for this group of proteins, the basic domain is involved in DNA-binding (Talanian et al., 1990, Science 249:769–771), while the leucine repeats in dimerization (O'Neil et al., 1990, Science 249:774–778). Another distinctive feature of the encoded protein is that its N-terminal region, from Ala-1 to Pro-107, has a net negative charge of 7. This region also contains a high proportion of serine and threonine. Domains of trans factors enriched in acidic residues and or hydroxy amino acids have been implicated in transcription activation (cf. Johnson and McKnight, 1989, Ann. Rev. Biochem 58:799–839). For convenience, the protein encoded by this partial cDNA is designated truncated TAF-1.

To determine how many genes in the tobacco genome are related to the TAF-1 gene, Southern blot hybridization were carried out using the 1.2 Kb EcoRI fragment of the TAF-1 partial cDNA (FIG. 2C) as a probe. Two hybridizing bands were obtained with genomic DNA digested with either HindIII (FIG. 2B, lane 1), or EcoRI (FIG. 2B, lane 2). These results suggest that TAF-1 is likely to be encoded by one or two genes.

6.2.3. DNA BINDING SPECIFICITY OF TRUNCATED TAF-1

To see whether the protein product encoded by p5a could indeed bind DNA, extracts were prepared from *E. coli* carrying the expression vector pSK(−) before and after IPTG induction. In this vector, the Met-22 of the partial TAF-1 coding sequence was presumably used as the initiator methionine to produce an N-terminal truncated TAF-1 of $Mr \approx 26,000$. The extracts were tested with motif I wild type and mutant tetramers in gel mobility-shift assays. FIG. 2D shows that the wild type tetramer formed specific complexes when incubated with extracts from IPTG-induced cells (lane 2), but not with extracts from uninduced cells (lane 1). Neither extracts gave any specific complexes with the mutant tetramer (FIG. 2D, lanes 3 and 4). These results indicate that the recombinant protein encoded by the p5a partial cDNA insert binds specifically to motif I and therefore, its full-length product, TAF-1, is a good candidate for the motif I factor. Because the wild type tetramer contains four copies of motif I, it was therefore, not surprising that multiple complexes were obtained with this probe (FIG. 2D, lane 2).

6.2.4. BINDING SITE SEQUENCE SPECIFICITY OF TAF-1

To define nucleotides in motif I critical for interaction with TAF-1 a set of motif I mutants (M1 to M5) (SEQ. ID NOS: 4–8) that contain successive 2-bp substitution mutations were synthesized. The ability of these mutants to bind the truncated TAF-1 was assessed by gel mobility-shift assays. Because the truncated TAF-1 contains the entire bZip domain, in these experiments it was assumed that its DNA-binding specificity is indistinguishable from that of the full length product. Mutations in the central six nucleotides of motif I (M2, M3 and M4) (SEQ. ID NOS: 5, 6 and 7) virtually abolished binding and mutations in the last two nucleotides (M5) (SEQ. ID NO: 8) severely reduced TAF-1 binding (FIG. 3). By contrast, mutant M1 (SEQ. ID NO: 4) which contains mutations in the first 2 nucleotides, showed an increased affinity for the same factor.

Detailed analysis of the M1 sequence revealed that it shares nine nucleotides with the 10-nucleotide palindromic sequence (PA) GCCACGTGGC (FIG. 4C) (SEQ. ID NO: 9), which is identical to the G-box motif found at −190 of the petunia rbcS-611 gene (Tumer et al., 1986, Nucleic Acids Research 14:3325– 3342). Because bZip proteins bind to their target DNA sites as dimers, it is reasonable to assume that TAF-1 might show a preference for palindromic sequences. To examine this possibility, the interaction of PA and the truncated TAF-1 was investigated by gel mobility-shift assay. These results demonstrate that the PA tetramer indeed showed a higher affinity for TAF-1 as compared to the wild type tetramer (FIG. 4A).

To assess the relative affinities of WT, PA, and M1-M5, for TAF-1 the wild type tetrameter was used as a probe and increasing amounts of unlabeled PA or mutant tetramers as competitors. FIG. 4B shows that approximately 50% competition was obtained with 200 ng of wild type while only 60 ng of M1 and 3 ng of PA were sufficient to give the same degree of competition. These results suggest that the binding affinity of TAF-1 for PA and M1 are about 66 and 3.3 times higher, respectively, than for WT. Mutant M5 was slightly less effective in this competition assay as compared to the WT. The remaining mutants M2, M3, and M4 were ineffective as competitors at concentrations of 200 ng or higher.

The results obtained from the competition experiments (FIG. 4B) are consistent with those obtained from direct binding (FIGS. 3 and 4A), and they are summarized in FIG. 4C. Comparison of the relative binding affinities with the nucleotide sequences of PA, WT, and the various mutants shows that the PA has the highest affinity for TAF-1. Moreover, the binding affinity appears to decrease with an increasing degree of nucleotide mismatch.

6.2.5. BINDING SITE SEQUENCE SPECIFICITY OF THE NUCLEAR MOTIF I FACTOR

Although both the nuclear motif I factor (FIG. 1C) and the recombinant TAF-1 (FIG. 2D) showed sequence-specific binding to motif I, it was not known whether they are indeed the same factor. To investigate this point, the binding site sequence requirement of nuclear motif I factor was determined by gel mobility-shift assays using motif I as a probe and the panel of mutants (FIG. 4C) (SEQ. ID NOS: 4–8) as competitors. Within the limit of sensitivity of this technique the result obtained with the nuclear factor (FIG. 4D) were about the same as those with the truncated TAF-1 (FIG. 4B). These results indicate that the full length TAF-1 is a good candidate for a nuclear motif I factor or is a major component of it.

6.2.6. TRUNCATED TAF-1 ALSO BINDS TO THE HEX MOTIF

The basic region of TAF-1 is strikingly homologous to the corresponding region of HBP-1 (FIG. 5A) (SEQ. ID NO: 18), a wheat DNA-binding protein that interacts with the conserved hexamer (hex) sequence located at −171 of the wheat histone H3 promoter (SEQ. ID NO: 40) (Tabata et al., 1989, Science 245:965–967). This observation prompted the examination of to examine whether the recombinant TAF-1 would also bind to this sequence. FIG. 6 shows that the truncated form of TAF-1 produced in *E. coli* could indeed bind to the −180 to −160 region of the wheat histone H3 promoter (lanes 1 and 2). The binding was dependent on the intact hex sequence since a 3-bp mutation in positions −168 to 170 greatly diminished the binding (lanes 3 and 4).

6.2.7. EXPRESSION PATTERN OF TAF-1 mRNA

FIG. 7, top panel, shows that the TAF-1 mRNA is expressed in roots but undetectable in stems and leaves. A longer exposure of the same autoradiogram, however, revealed a faint band of the same size in these two samples. It is estimated that there is about 10–20 times more TAF-1 mRNA in roots as compared to stems and leaves. As a control, the mRNA of the constitutively expressed $\beta$-ATPase gene (Boutry and Chua, 1985, EMBO J. 4:2159–2165) is present at approximately twofold higher roots than in the other two organs (FIG. 7, bottom panel).

Because the size of the TAF-1 mRNA is 2.2 Kb, it is estimated that about 0.8 Kb of TAF-1 sequences are missing from the partial cDNA clone which encodes the 3' portion of the gene.

6.2.8 TAF-1 IS A TRANS-ACTIVATOR

To see whether the recombinant TAF would function as a transcription activator in vivo, double stranded oligonucleotides were synthesized containing either four copies of WT motif I sequence or four copies of a motif I mutant sequence. These tetramers were separately placed upstream of the −90 CaMV 35S promoter (Benfey et al., 1989, EMBO J.8:2195–2202). In both cases, the bacterial $\beta$-glucuronidase (GUS) coding sequence was used as the reporter gene. These chimeric genes were transferred into tobacco and several independent transgenic plants for each construct were analyzed for GUS activity.

The WT motif I tetramer conferred little or no activity in leaves of transgenic plants, while the mutant tetramer was inactive (Table II). Addition of ABA had no noticeable effect on either the GUS activity (Table II) or mRNA levels in leaves of transgenic plants harboring either construct.

TABLE II

A Truncated TAF-1 can Trans-Activiate the Expression of a GUS Reporter Gene Linked To a Motif I Tetramer.

|  | (A) WT × 4 | | (B) MU × 4 | |
| --- | --- | --- | --- | --- |
|  | −ABA | +ABA | −ABA | +ABA |
| no bombardment | 250 | 383 | 237 | 230 |
| vector control | 500 | 500 | 550 | 600 |
| 35S partial TAF-1 cDNA | 4,300 | 4,150 | 515 | 633 |

Footnote to Table II: Adult leaves (~8 cm×4 cm) from transgenic plants containing either the motif I tretramer fused to X-GUS90 (A) or the mutant tetramer fused to X-GUS90 (B) were cut into two sections. One section was bombarded with tungsten particles coated with pMON505 (Benfey et al., 1989, EMBOJ.8:2195–2202) while the other section with a pMON505 derivative containing a 35S:5a-cDNA chimeric gene. The latter was comprised of the CaMV 35S promoter (−343 to +8), the partial TAF-1 cDNA and the rbcS-E9 3' polyadenylation signal. Afterward the leaf sections were incubated in the dark in water or $10^{-4}$M ABA for 24 hr at room temperature. Non-bombarded leaf sections were used as controls. GUS activities were measured according to Jefferson et al. (1987, EMBO J. 6:3901–3907) and expressed as pmoles 4-methyl umbelliferone/mg protein/min. Results shown are representative of four independent experiments for (A) and three independent experiments for (B). (End of Footnote to Tables II)

The low expression level in leaves conferred by motif I could be due to a reduced concentration of its cognate transcription activator in cells of this organ. This is also consistent with the low TAF-1 mRNA in leaf (FIG. 7). If the truncated TAF-1 binds to motif I in vivo and functions as a trans-activator, it should be possible to elevate GUS expression in leaves by over-expression of TAF-1. To test this hypothesis, a chimeric gene was constructed comprised of the CaMV 35S promoter (−343 to +8) and the partial TAF-1 cDNA coding sequence. Plasmid DNA containing this chimeric gene was introduced by high velocity bombardment into cells of transgenic leaves carrying the motif I tetramer-GUS transgene. Table II supra shows that bombardment of the 35S/TAF-1 effector plasmid indeed increased GUS expression in the leaves by about 10- to 15- fold while the vector DNA alone gave less than 2-fold stimulation. Because only a fraction of the leaf cells received the effector plasmid, it is likely that the actual amount of activation with the 35S/TAF-1 construct was higher. The GUS expression was dependent on the ability of TAF-1 to bind to motif I, since leaves of transgenic plants carrying the mutant motif I tetramer failed to respond to the same effector plasmid. Experiments were conducted to test whether the GUS expression in leaves conferred by motif I and TAF-1 was influenced in any way be ABA treatment. Table II shows that the GUS activity was not significantly different between the ABA-treated and the control samples.

Although the invention is described with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

What is claimed is:

1. A substantially pure nucleotide sequence encoding a plant transactivating factor, TAF-1, which factor has the amino acid sequence depicted in FIG. 2A (SEQ. ID NO: 1) from amino acid residue number 1 to amino acid residue 265 of a truncated portion of said amino acid sequence that binds to motif I and functions as a transactivator to increase the expression of coding sequences operably joined to motif I.

2. A recombinant DNA vector containing the TAF-1 nucleotide sequence of claim 1.

3. The recombinant DNA vector of claim 2 in which the TAF-1 nucleotide sequence is controlled by a second sequence that regulates the expression of the TAF-1 neucleotide sequence in a host cell.

4. A host cell containing a heterologous nucleotide sequence encoding a plant transactivating factor, TAF-1, which factor has the amino acid sequence depicted in FIG. 2A (SEQ. ID NO: 1) from amino acid residue number 1 to amino acid residue 265 or truncated portion of said amino acid sequence that binds to motif I and functions as a transactivator to increase the expression of coding sequences operably joined to motif I.

5. The host cell of claim 4 in which the TAF-1 nucleotide sequence is controlled by a second sequence that regulates expression of the TAF-1 nucleotide sequence in the host cell.

6. The host cell of claim 5 which also contains a gene of interest, the expression of which is controlled by a regulatory sequence that contains a binding site for TAF-1, so that expression of the gene interest is increased when TAF-1 is expressed by the host cell.

7. The host cell of claim 4, 5, or 6 which is a cultured plant cell.

8. The host cell of claim 6 in which the regulatory sequence controlling expression of the gene of interest contains one or more copies of the nucleotide sequence: RTACGTGGR, in which R represents an A or G nucleotide.

9. The host cell of claim 6 in which the regulatory sequence controlling the gene of interest contains one or more copies of the nucleotide sequence (SEQ. ID NO: 9) GCCACGTGGC.

10. The host cell of claims 6 in which the regulatory sequence controlling the gene of interest contains one or more copies of the nucleotide sequence (SEQ. ID NO: 10)
GCAACGTGGC.

11. The host cell of claim 6 in which the regulatory sequence controlling the gene of interest contains one or more copies of the nucleotides sequence (SEQ. ID NO: 11) GGTACGTGGC.

12. The host cell of claim 6 in which the regulatory sequence controlling the gene of interest contains one or more copies of the nucleotide sequence (SEQ. ID NO: 12) CGTACGTGGG.

13. A transgenic plant containing a heterologous nucleotide sequence encoding a plant transactivating factor, TAF-1, which factor has the amino acid sequence depicted in FIG. 2A (SEQ. ID NO: 1) from amino acid residue number 1 to amino acid residue 265 or a truncated portion of said amine acid sequence that binds to motif I and functions as a transactivator to increase the expression of coding sequences operably joined to motif I.

14. The transgenic plant of claim 13 in which the TAF-1 nucleotide sequence is controlled by a second sequence that regulates expression of the TAF-1 nucleotide sequence in the transgenic plant.

15. The transgenic plant of claim 14 which also contains a gene of interest, the expression of which is controlled by a regulatory sequence that contains a binding site for TAF-1, so that expression of the gene of interest is increased when TAF-1 is expressed by the transgenic plant.

16. The transgenic plant of claim 15 in which the regulatory sequence controlling expression of the gene of interest contains one or more copies of the nucleotide sequence RTACGTGGR in which R represents an A or G nucleotide.

17. The transgenic plant of claim 15 in which the regulatory sequence controlling expression of the gene of interest contains one or more copies of the nucleotide sequence (SEQ. ID NO: 9)
GCCACGTGGC.

18. The transgenic plant of claim 16 in which the regulatory sequence controlling expression of the gene of interest contains one or more copies of the nucleotide sequence (SEQ. ID NO: 10)
GCAACGTGGC.

19. The transgenic plant of claim 16 in which the regulatory sequence controlling expression of the gene of interest contains one or more copies of the nucleotide sequence (SEQ. ID NO: 11)
GGTACGTGGC.

20. The transgenic plant of claim 15 in which the regulatory sequence controlling expression of the gene of interest contains one or more copies of the nucleotide sequence (SEQ. ID NO: 12)
CGTACGTGGG.

21. A substantially pure nucleotide sequence encoding a plant transactivating factor, TAF-1, which sequence has the nucleotide sequence depicted in FIG. 2A (SEQ. ID NO: 1) from nucleotide residue number 1 to nucleotide residue number 903 or a truncated portion of said nucleotide sequence encoding a truncated portion of said factor that binds to motif I and functions as a transactivator to increase the expression of coding sequences operably joined to motif I.

22. A recombinant DNA vector containing the transactivating factor nucleotide sequence of claim 21.

23. A recombinant DNA vector of claim 22 in which the transactivating factor neucleotide sequence is controlled by a promoter sequence that regulates the expression of the transactivating factor nucleotide sequence in a host cell.

24. A host cell containing a recombinant gene construct comprising the nucleotide sequence of claim 21, which is not naturally associated with said host cell.

25. A transgenic plant containing a recombinant gene construct comprising the nucleotide sequence of claim 21 which is not naturally associated with said transgenic plant.

26. A host cell containing a DNA vector of claim 22 or 23.

27. A transgenic plant containing a DNA vector of claim 22 or 23.

* * * * *

SEQUENCE LISTING ( 1 ) GENERAL INFORMATION:

( i i i ) NUMBER OF SEQUENCES: 45

( 2 ) INFORMATION FOR SEQ ID NO:1:

( i ) SEQUENCE CHARACTERISTICS:
        ( A ) LENGTH: 1338 base pairs
        ( B ) TYPE: nucleic acid
        ( C ) STRANDEDNESS: single
        ( D ) TOPOLOGY: unknown ( i i ) MOLECULE TYPE: cDNA ( i x ) FEATURE:
    ( A ) NAME/KEY: CDS
    ( B ) LOCATION: 9..803

( x i ) SEQUENCE DESCRIPTION: SEQ ID NO:1:

```
GGAATTCC GCT CAT GGT GGC GTT TAT GCA CAT CCT GGA GTT CCA ATT GGA        50
         Ala His Gly Gly Val Tyr Ala His Pro Gly Val Pro Ile Gly
          1           5                  10

TCT CAC CCT CCA GGA CAT GGG ATG GCA ACA TCT CCT GCT GTC AGC CAA         98
Ser His Pro Pro Gly His Gly Met Ala Thr Ser Pro Ala Val Ser Gln
 15              20                  25                  30

GCC ATG GAT GGT GCT TCT TTG AGT TTG GAT GCA TCT GCT AAG TCT TCA        146
Ala Met Asp Gly Ala Ser Leu Ser Leu Asp Ala Ser Ala Lys Ser Ser
             35                  40                  45

GAG AAT TCT GAT CGA GGC TTG CTG GCA ATG TCA CTA GGA AAT GGC AGT        194
Glu Asn Ser Asp Arg Gly Leu Leu Ala Met Ser Leu Gly Asn Gly Ser
                 50                  55                  60

GCT GAC AAC ATT GAA GGT GGA GCG GAC CAT GGA AAT TCA CAG AGT GGG        242
Ala Asp Asn Ile Glu Gly Gly Ala Asp His Gly Asn Ser Gln Ser Gly
             65                  70                  75

GAC ACT GAA GAT TCA ACT GAT GGA AGT GAC ACA AAT GGA GCT GGG GTC        290
Asp Thr Glu Asp Ser Thr Asp Gly Ser Asp Thr Asn Gly Ala Gly Val
 80                  85                  90

AGT GAG AGA AGT AAG AAA CGA AGC CGT GAG ACA ACT CCT GAT AAC TCT        338
Ser Glu Arg Ser Lys Lys Arg Ser Arg Glu Thr Thr Pro Asp Asn Ser
 95                 100                 105                 110

GGT GAT AGT AAG AGT CAC TTA CGA CGA TGT CAA CCT ACT GGG GAA ATA        386
Gly Asp Ser Lys Ser His Leu Arg Arg Cys Gln Pro Thr Gly Glu Ile
                 115                 120                 125

AAT GAT GAT TCT GAG AAG GCA ATT GTG GCT GTT CGT CCT GGT AAG GTA        434
Asn Asp Asp Ser Glu Lys Ala Ile Val Ala Val Arg Pro Gly Lys Val
             130                 135                 140

GGG GAG AAA GTG ATG GGA ACT GTA CTT TCT CCT AGC ATG ACA ACA ACT        482
Gly Glu Lys Val Met Gly Thr Val Leu Ser Pro Ser Met Thr Thr Thr
             145                 150                 155

TTG GAA ATG AGA AAT CCT GCT AGT ACA CAT TTG AAA GCT AGC CCA ACT        530
Leu Glu Met Arg Asn Pro Ala Ser Thr His Leu Lys Ala Ser Pro Thr
 160                 165                 170

AAT GTT TCA CAA CTC AGC CCT GCA CTG CCA AAT GAA GCC TGG TTA CAG        578
Asn Val Ser Gln Leu Ser Pro Ala Leu Pro Asn Glu Ala Trp Leu Gln
175                 180                 185                 190

AAT GAA CGT GAG CTG AAG CGG GAG AAA AGG AAA CAG TCT AAT CGG GAA        626
Asn Glu Arg Glu Leu Lys Arg Glu Lys Arg Lys Gln Ser Asn Arg Glu
                 195                 200                 205

TCT GCA AGG CGA TCA AGA TTG AGA AAA CAG GCT GAA GCT GAA GAA TTG        674
Ser Ala Arg Arg Ser Arg Leu Arg Lys Gln Ala Glu Ala Glu Glu Leu
             210                 215                 220

GCA ATA CGA GTT CAG TCT TTA ACA GCG GAA AAC ATG ACA CTC AAA TCT        722
Ala Ile Arg Val Gln Ser Leu Thr Ala Glu Asn Met Thr Leu Lys Ser
             225                 230                 235

GAG ATA AAC AAA TTA ATG GAG AAC TCA GAG AAA CTG AAG CTA GAA AAT        770
Glu Ile Asn Lys Leu Met Glu Asn Ser Glu Lys Leu Lys Leu Glu Asn
 240                 245                 250

GCT GCT TTA ATG GAG AGA CTG AAA ATG AAC AGC TAGGCCAGAC AGAAGAAGTG      823
Ala Ala Leu Met Glu Arg Leu Lys Met Asn Ser
 255                 260                 265

AGTTTAGGTA AGATTGATGA TAAGAGGCTG CAACCTGTAG GCACGGCAAA CCTACTAGCA      883

AGAGTCAACA ACTCTGGTTC CTCGGATAGA GCAAACGAGG AGATTGAAGT TTATGAGAAC      943
```

-continued

```
AATAGTTCTG GAGCAAAGCT TCATCAACTA CTCGATTCCA GTCCCAGAAC TGATGCAGTG      1003
GCTGCTGGGT GATCGATGGT ACACCCCCAA CTTTGAGATC TTACATTTTA GTCTGATTAT      1063
GTAATTTTGG CGTAATTATA AGTCCAAAGT TACTGCTAAC TGCGGGAGAG GAACAGAATG      1123
GAACAGCTAA ATAGGATTAT GGAACTTACG GGATTCTAAT TTTACCTAAT TGTAGTTTAC      1183
GTGTCGGAAG AACTGATGTG TGCTTTTATA CTTTCTTTT CTTCCTTTT TCCCCTTTT        1243
CACCTCAGAG AGGGATGTTG GCCATAATAG TTTATGTAAG TTTGTAATCT TCGACATGTA      1303
TAAGCTTTGA TTGAGGAAAA AAAAAAAGG AATTC                                  1338
```

( 2 ) INFORMATION FOR SEQ ID NO:2:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: unknown ( i i ) MOLECULE TYPE: TAF-1 binding motif ( x i ) SEQUENCE DESCRIPTION: SEQ ID NO:2:

GTACGTGGCG          10

( 2 ) INFORMATION FOR SEQ ID NO:3:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: unknown ( i i ) MOLECULE TYPE: TAF-1 binding motif ( x i ) SEQUENCE DESCRIPTION: SEQ ID NO:3:

TGACTGTTCT          10

( 2 ) INFORMATION FOR SEQ ID NO:4:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: unknown ( i i ) MOLECULE TYPE: TAF-1 binding motif ( x i ) SEQUENCE DESCRIPTION: SEQ ID NO:4:

CAACGTGGCG          10

( 2 ) INFORMATION FOR SEQ ID NO:5:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: unknown ( i i ) MOLECULE TYPE: TAF-1 binding motif ( x i ) SEQUENCE DESCRIPTION: SEQ ID NO:5:

GTTGGTGGCG          10

( 2 ) INFORMATION FOR SEQ ID NO:6:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: unknown ( i i ) MOLECULE TYPE: TAF-1 binding motif ( x i ) SEQUENCE DESCRIPTION: SEQ ID NO:6:

GTACCAGGCG 10

( 2 ) INFORMATION FOR SEQ ID NO:7:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: unknown ( i i ) MOLECULE TYPE: TAF-1 binding motif ( x i ) SEQUENCE DESCRIPTION: SEQ ID NO:7:

GTACGTCCCG 10

( 2 ) INFORMATION FOR SEQ ID NO:8:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: unknown ( i i ) MOLECULE TYPE: TAF-1 binding motif ( x i ) SEQUENCE DESCRIPTION: SEQ ID NO:8:

GTACGTGGGC 10

( 2 ) INFORMATION FOR SEQ ID NO:9:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: unknown ( i i ) MOLECULE TYPE: TAF-1 binding motif ( x i ) SEQUENCE DESCRIPTION: SEQ ID NO:9:

GCCACGTGGC 10

( 2 ) INFORMATION FOR SEQ ID NO:10:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: unknown ( i i ) MOLECULE TYPE: TAF-1 binding motif ( x i ) SEQUENCE DESCRIPTION: SEQ ID NO:10:

GCAACGTGGC 10

( 2 ) INFORMATION FOR SEQ ID NO:11:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: unknown ( i i ) MOLECULE TYPE: TAF-1 binding motif ( x i ) SEQUENCE DESCRIPTION: SEQ ID NO:11:

GGTACGTGGC 10

( 2 ) INFORMATION FOR SEQ ID NO:12:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: unknown ( i i ) MOLECULE TYPE: TAF-1 binding motif ( x i ) SEQUENCE DESCRIPTION: SEQ ID NO:12:

CGTACGTGGG        10

( 2 ) INFORMATION FOR SEQ ID NO:13:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: unknown ( i i ) MOLECULE TYPE: TAF-1 binding motif ( x i ) SEQUENCE DESCRIPTION: SEQ ID NO:13:

GGTTGGTGGC        10

( 2 ) INFORMATION FOR SEQ ID NO:14:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: unknown ( i i ) MOLECULE TYPE: TAF-1 binding motif ( x i ) SEQUENCE DESCRIPTION: SEQ ID NO:14:

GGTACCAGGC        10

( 2 ) INFORMATION FOR SEQ ID NO:15:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: unknown ( i i ) MOLECULE TYPE: TAF-1 binding motif ( x i ) SEQUENCE DESCRIPTION: SEQ ID NO:15:

GGTACGTCCC        10

( 2 ) INFORMATION FOR SEQ ID NO:16:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:16:

Lys Arg Glu Lys Arg Lys Gln Ser Asn Arg Glu Ser Ala Arg Arg Ser
1               5                   10                  15

Arg Leu Arg Lys
            20

( 2 ) INFORMATION FOR SEQ ID NO:17:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: unknown ( i i ) MOLECULE TYPE: peptide ( x i ) SEQUENCE DESCRIPTION: SEQ ID NO:17:

Lys Arg Glu Arg Arg Lys Gln Ser Asn Arg Glu Ser Ala Arg Arg Ser
1               5                   10                  15

Arg Leu Arg Lys
            20

( 2 ) INFORMATION FOR SEQ ID NO:18:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: unknown ( i i ) MOLECULE TYPE: peptide ( x i ) SEQUENCE DESCRIPTION: SEQ ID NO:18:

Lys Lys Gln Lys Arg Lys Leu Ser Asn Arg Glu Ser Ala Arg Arg Ser
1               5                   10                  15

Arg Leu Arg Lys
            20

( 2 ) INFORMATION FOR SEQ ID NO:19:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: unknown ( i i ) MOLECULE TYPE: peptide ( x i ) SEQUENCE DESCRIPTION: SEQ ID NO:19:

Arg Arg Glu Lys Arg Arg Leu Ser Asn Arg Glu Ser Ala Arg Arg Ser
1               5                   10                  15

Arg Leu Arg Lys
            20

( 2 ) INFORMATION FOR SEQ ID NO:20:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: unknown ( i i ) MOLECULE TYPE: peptide ( x i ) SEQUENCE DESCRIPTION: SEQ ID NO:20:

Arg Val Arg Lys Arg Lys Glu Ser Asn Arg Glu Ser Ala Arg Arg Ser
1               5                   10                  15

Arg Tyr Arg Lys
            20

( 2 ) INFORMATION FOR SEQ ID NO:21:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: unknown ( i i ) MOLECULE TYPE: peptide ( x i ) SEQUENCE DESCRIPTION: SEQ ID NO:21:

Lys Val Leu Arg Arg Leu Ala Gln Asn Arg Glu Ala Ala Arg Lys Ser
1               5                   10                  15
Arg Leu Arg Lys
            20

( 2 ) INFORMATION FOR SEQ ID NO:22:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:22:

Lys Lys Arg Ala Arg Leu Val Arg Asn Arg Glu Ser Ala Gln Leu Ser
1               5                   10                  15
Arg Gln Arg Lys
            20

( 2 ) INFORMATION FOR SEQ ID NO:23:

( i ) SEQUENCE CHARACTERISTICS:
        ( A ) LENGTH: 42 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:23:

Gln Ala Glu Ala Glu Glu Leu Ala Ile Gln Val Gln Ser Leu Thr Ala
1               5                   10                  15
Glu Asn Asn Thr Leu Lys Ser Glu Ile Asn Lys Leu Met Glu Asn Ser
                20                  25                  30
Glu Lys Leu Lys Leu Glu Asn Ala Ala Leu
            35                  40

( 2 ) INFORMATION FOR SEQ ID NO:24:

( i ) SEQUENCE CHARACTERISTICS:
        ( A ) LENGTH: 42 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:24:

Gln Gln Glu Cys Glu Glu Leu Ala Gln Lys Val Ser Glu Leu Thr Ala
1               5                   10                  15
Ala Asn Gly Thr Leu Arg Ser Glu Leu Asp Gln Leu Lys Lys Asp Cys
                20                  25                  30
Lys Thr Met Glu Thr Glu Asn Lys Gln Leu
            35                  40

( 2 ) INFORMATION FOR SEQ ID NO:25:

( i ) SEQUENCE CHARACTERISTICS:
        ( A ) LENGTH: 42 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:25:

Gln Ala Glu Cys Glu Glu Leu Gly Gln Arg Ala Glu Ala Leu Lys Ser
1               5                   10                  15

Glu Asn Ser Ser Leu Arg Ile Glu Leu Asp Arg Ile Lys Lys Glu Tyr
            20                  25                  30

Glu Glu Leu Leu Ser Lys Asn Thr Ser Leu
            35              40

( 2 ) INFORMATION FOR SEQ ID NO:26:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:26:

Gln Gln His Leu Asp Glu Leu Val Gln Glu Val Ala Arg Leu Gln Ala
1               5                   10                  15

Asp Asn Ala Arg Val
            20

( 2 ) INFORMATION FOR SEQ ID NO:27:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: unknown ( i i ) MOLECULE TYPE: G-box binding motif ( x i ) SEQUENCE DESCRIPTION: SEQ ID NO:27:

TCTTACACGT GGCAYY                                                16

( 2 ) INFORMATION FOR SEQ ID NO:28:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: unknown ( i i ) MOLECULE TYPE: TAF-1 binding motif ( x i ) SEQUENCE DESCRIPTION: SEQ ID NO:28:

GTACGTGGCG                                                       10

( 2 ) INFORMATION FOR SEQ ID NO:29:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: unknown ( i i ) MOLECULE TYPE: TAF-1 binding motif ( x i ) SEQUENCE DESCRIPTION: SEQ ID NO:29:

TTCGGCCACG TCACCAATCC G                                          21

( 2 ) INFORMATION FOR SEQ ID NO:30:

( i ) SEQUENCE CHARACTERISTICS:
        ( A ) LENGTH: 19 base pairs (B) TYPE: nucleic acid
(C) STRANDEDNESS: double
(D) TOPOLOGY: unknown (ii) MOLECULE TYPE: TAF-1 binding motif (xi) SEQUENCE DESCRIPTION: SEQ ID NO:30:

TTCGGCCACG TCCAATCCG  19

(2) INFORMATION FOR SEQ ID NO:31:

(i) SEQUENCE CHARACTERISTICS:
(A) LENGTH: 10 base pairs
(B) TYPE: nucleic acid
(C) STRANDEDNESS: double
(D) TOPOLOGY: unknown (ii) MOLECULE TYPE: TAF-1 binding motif (xi) SEQUENCE DESCRIPTION: SEQ ID NO:31:

GCCACGTGTC  10

(2) INFORMATION FOR SEQ ID NO:32:

(i) SEQUENCE CHARACTERISTICS:
(A) LENGTH: 10 base pairs
(B) TYPE: nucleic acid
(C) STRANDEDNESS: double
(D) TOPOLOGY: unknown (ii) MOLECULE TYPE: TAF-1 binding motif (xi) SEQUENCE DESCRIPTION: SEQ ID NO:32:

TCCACGTGGC  10

(2) INFORMATION FOR SEQ ID NO:33:

(i) SEQUENCE CHARACTERISTICS:
(A) LENGTH: 10 base pairs
(B) TYPE: nucleic acid
(C) STRANDEDNESS: double
(D) TOPOLOGY: unknown (ii) MOLECULE TYPE: TAF-1 binding motif (xi) SEQUENCE DESCRIPTION: SEQ ID NO:33:

TACACGTGGC  10

(2) INFORMATION FOR SEQ ID NO:34:

(i) SEQUENCE CHARACTERISTICS:
(A) LENGTH: 10 base pairs
(B) TYPE: nucleic acid
(C) STRANDEDNESS: double
(D) TOPOLOGY: unknown (ii) MOLECULE TYPE: TAF-1 binding motif (xi) SEQUENCE DESCRIPTION: SEQ ID NO:34:

CAGACGTGGC  10

(2) INFORMATION FOR SEQ ID NO:35:

(i) SEQUENCE CHARACTERISTICS:
(A) LENGTH: 10 base pairs
(B) TYPE: nucleic acid
(C) STRANDEDNESS: double
(D) TOPOLOGY: unknown (ii) MOLECULE TYPE: TAF-1 binding motif (xi) SEQUENCE DESCRIPTION: SEQ ID NO:35:

GCCACGTGGA                                                                                          10

( 2 ) INFORMATION FOR SEQ ID NO:36:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: unknown ( i i ) MOLECULE TYPE: TAF-1 binding motif ( x i ) SEQUENCE DESCRIPTION: SEQ ID NO:36:

GTCACGTGCC                                                                                          10

( 2 ) INFORMATION FOR SEQ ID NO:37:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: unknown ( i i ) MOLECULE TYPE: TAF-1 binding motif ( x i ) SEQUENCE DESCRIPTION: SEQ ID NO:37:

TCCACGTGGC                                                                                          10

( 2 ) INFORMATION FOR SEQ ID NO:38:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: unknown ( i i ) MOLECULE TYPE: TAF-1 binding motif ( x i ) SEQUENCE DESCRIPTION: SEQ ID NO:38:

TACACGTGGC                                                                                          10

( 2 ) INFORMATION FOR SEQ ID NO:39:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: unknown ( i i ) MOLECULE TYPE: TAF-1 binding motif ( x i ) SEQUENCE DESCRIPTION: SEQ ID NO:39:

GCCACGTGAC                                                                                          10

( 2 ) INFORMATION FOR SEQ ID NO:40:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: unknown ( i i ) MOLECULE TYPE: TAF-1 binding motif ( x i ) SEQUENCE DESCRIPTION: SEQ ID NO:40:

GTGACGTGGC                                                                                          10

( 2 ) INFORMATION FOR SEQ ID NO:41:

( i ) SEQUENCE CHARACTERISTICS:

( A ) LENGTH: 10 base pairs
        ( B ) TYPE: nucleic acid
        ( C ) STRANDEDNESS: double
        ( D ) TOPOLOGY: unknown ( i i ) MOLECULE TYPE: TAF-1 binding motif ( x i ) SEQUENCE DESCRIPTION: SEQ ID NO:41:

GACACGTGGC 10

( 2 ) INFORMATION FOR SEQ ID NO:42:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: unknown ( i i ) MOLECULE TYPE: TAF-1 binding motif ( x i ) SEQUENCE DESCRIPTION: SEQ ID NO:42:

GGTACGTGGC 10

( 2 ) INFORMATION FOR SEQ ID NO:43:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: unknown ( i i ) MOLECULE TYPE: TAF-1 binding motif ( x i ) SEQUENCE DESCRIPTION: SEQ ID NO:43:

GCCACGTGGC 10

10

( 2 ) INFORMATION FOR SEQ ID NO:44:

( i ) SEQUENCE CHARACTERISTICS:
        ( A ) LENGTH: 11 base pairs
        ( B ) TYPE: nucleic acid
        ( C ) STRANDEDNESS: double
        ( D ) TOPOLOGY: unknown ( i i ) MOLECULE TYPE: G-box-like binding motif ( x i ) SEQUENCE DESCRIPTION: SEQ ID NO:44:

GGACACGTGG C 11

( 2 ) INFORMATION FOR SEQ ID NO:45:

( i ) SEQUENCE CHARACTERISTICS:
        ( A ) LENGTH: 11 base pairs
        ( B ) TYPE: nucleic acid
        ( C ) STRANDEDNESS: double
        ( D ) TOPOLOGY: unknown ( i i ) MOLECULE TYPE: G-box-like binding motif ( x i ) SEQUENCE DESCRIPTION: SEQ ID NO:45:

GCACACGTGC C 11